US012758896B2

(12) United States Patent
Doherty et al.

(10) Patent No.: US 12,758,896 B2
(45) Date of Patent: Oct. 13, 2026

(54) HIGH-THROUGHPUT CHROMATOGRAPHY SCREENING FOR EXTRACELLULAR VESICLES

(71) Applicant: LONZA SALES AG, Basel (CH)

(72) Inventors: Michael Doherty, Somerville, MA (US); Aaron Noyes, Melrose, MA (US); Andrew Wood, Concord, MA (US)

(73) Assignee: LONZA SALES AG, Basel (CH)

( * ) Notice: Subject to any disclaimer, the term of this patent is extended or adjusted under 35 U.S.C. 154(b) by 833 days.

(21) Appl. No.: 17/774,774

(22) PCT Filed: Nov. 5, 2020

(86) PCT No.: PCT/US2020/059135
§ 371 (c)(1),
(2) Date: May 5, 2022

(87) PCT Pub. No.: WO2021/092193
PCT Pub. Date: May 14, 2021

(65) Prior Publication Data
US 2022/0390437 A1 Dec. 8, 2022

Related U.S. Application Data

(60) Provisional application No. 62/931,089, filed on Nov. 5, 2019.

(51) Int. Cl.
*G01N 33/50* (2006.01)
*B01D 15/38* (2006.01)
(Continued)

(52) U.S. Cl.
CPC ..... *G01N 33/5076* (2013.01); *B01D 15/3828* (2013.01); *G01N 21/49* (2013.01); *G01N 21/6486* (2013.01); *B01D 2221/10* (2013.01)

(58) Field of Classification Search
CPC .......................... B01D 15/08; B01D 15/3828; B01D 2221/10; G01N 21/33; G01N 21/49; G01N 21/51; G01N 21/6486; G01N 33/5076
See application file for complete search history.

(56) References Cited

U.S. PATENT DOCUMENTS 10,195,290 B1 2/2019 Dooley et al.
2013/0078658 A1 3/2013 Park et al.
(Continued)

FOREIGN PATENT DOCUMENTS

WO 2012/087241 A1 6/2012
WO 2018/112154 A1 6/2018
(Continued)

OTHER PUBLICATIONS

Gudbergsson et al., "Systematic review of factors influencing extracellular vesicle yield from cell cultures," Cytotechnology 68:579-592 (2015).
(Continued)

*Primary Examiner* — Dirk R Bass
(74) *Attorney, Agent, or Firm* — MEDLER FERRO WOODHOUSE & MILLS PLLC

(57) ABSTRACT

The present disclosure relates to high-throughput screening methods for identifying one or more chromatography operational parameters (e.g., binding parameters) and/or reagents for purifying EVs (e.g., exosomes) from a sample using chromatography. Also disclosed herein are methods for improving one or more aspects of EV (e.g., exosome) purification, e.g., improving EV yield, increasing EV ligand density, and/or reducing impurity recovery.

17 Claims, 11 Drawing Sheets

(51) Int. Cl.
*G01N 21/49* (2006.01)
*G01N 21/64* (2006.01)

(56) References Cited

U.S. PATENT DOCUMENTS

| | | | | |
|---|---|---|---|---|
| 2019/0085284 | A1* | 3/2019 | Villiger | C12P 1/00 |
| 2020/0284770 | A1* | 9/2020 | Gho | G01N 33/5076 |
| 2020/0330899 | A1* | 10/2020 | Jones | B01D 15/3804 |

FOREIGN PATENT DOCUMENTS

| | | | | |
|---|---|---|---|---|
| WO | 2019/060629 A1 | | 3/2019 | |
| WO | WO-2019066501 A1 | * | 4/2019 | G01N 33/58 |
| WO | 2019/099942 A1 | | 5/2019 | |
| WO | WO-2019133842 A1 | * | 7/2019 | B01D 15/34 |

OTHER PUBLICATIONS

Lobb et al., "Optimized exosome isolation protocol for cell culture supernatant and human plasma," Journal of Extracellular Vesicles 4:27031 (2015).
International Search Report in PCT/US2020/059135 , dated Apr. 14, 2021.

* cited by examiner

FIG. 5A

| Wash Buffer | | |
|---|---|---|
| Condition # | Excipient/Salt | Concentration (M or %) |
| 1 | Low pH Buffer A | 0.1 |
| 2 | | 0.5 |
| 3 | Low pH Buffer B | 0.1 |
| 4 | | 0.5 |
| **5** | High pH Buffer A | 0.1 |
| **6** | | 0.5 |
| **7** | Salt A | **0.5** |
| **8** | | 0.625 |
| 9 | | 0.75 |
| 10 | | 0.875 |
| 11 | **Control** | **0.5** |
| 12 | Salt B | 0.1 |
| 13 | | 0.5 |
| 14 | Salt C | 0.1 |
| 15 | | 0.5 |
| 16 | Salt D | 0.1 |
| 17 | | 0.5 |
| 18 | Polymer A | 0.001% |
| 19 | | 0.005% |
| 20 | | 0.010% |
| 21 | Amino Acid A | 0.1 |
| 22 | | 0.5 |
| 23 | | 1 |
| 24 | Amino Acid B | 0.1 |
| 25 | | 0.5 |
| 26 | Chelator A | 0.1 |
| 27 | | 0.25 |
| 28 | Salt E | 0.1 |
| 29 | | 0.2 |
| 30 | | 0.3 |
| 31 | Chaotrope A | 0.5 |
| 32 | | 1 |
| 33 | | 2 |
| 34 | Chaotrope B | 0.1 |
| 35 | | 0.25 |
| 36 | | 0.5 |
| 37 | Surfactant A | 0.1 |
| 38 | | 1 |
| 39 | | 0.1 |
| 40 | | 1 |

FIG. 6A

| | F/T A280 (% Recovery) | | | | | |
|---|---|---|---|---|---|---|
| | pH 6.0 | pH 6.5 | pH 7.0 | pH 7.5 | pH 8.0 | pH 8.5 |
| 0.4M NaCl | 58% | 53% | 56% | 58% | 58% | 60% |
| 0.6M NaCl | 58% | 58% | 64% | 64% | 65% | 66% |
| 0.8M NaCl | 62% | 60% | 67% | 68% | 68% | 70% |
| 1.0M NaCl | 62% | 63% | 71% | 71% | 72% | 73% |
| 1.2M NaCl | 64% | 65% | 72% | 72% | 72% | 75% |
| 1.4M NaCl | 64% | 68% | 74% | 74% | 75% | 77% |
| 1.6M NaCl | 63% | 66% | 74% | 73% | 73% | 73% |
| 1.8M NaCl | 64% | 70% | 76% | 70% | 80% | 75% |

FIG. 6B

| | SEC-HPLC (% Recovery) | | | | | |
|---|---|---|---|---|---|---|
| | pH 6.0 | pH 6.5 | pH 7.0 | pH 7.5 | pH 8.0 | pH 8.5 |
| 0.4M NaCl | 46% | 52% | 54% | 53% | 50% | 56% |
| 0.6M NaCl | 56% | 53% | 64% | 66% | 66% | 69% |
| 0.8M NaCl | 61% | 60% | 74% | 76% | 80% | 83% |
| 1.0M NaCl | 62% | 69% | 83% | 87% | 86% | 86% |
| 1.2M NaCl | 66% | 71% | 84% | 81% | 87% | 86% |
| 1.4M NaCl | 68% | 79% | 86% | 86% | 88% | 89% |
| 1.6M NaCl | 75% | 87% | 89% | 93% | 92% | 92% |
| 1.8M NaCl | 74% | 82% | 83% | 87% | 90% | 89% |

FIG. 6C

| | Proteoglycan Impurity (ng/mL) | | | | | |
|---|---|---|---|---|---|---|
| | pH 6.0 | pH 6.5 | pH 7.0 | pH 7.5 | pH 8.0 | pH 8.5 |
| 0.4M NaCl | 0 | 0 | 25 | 41 | 75 | 68 |
| 0.6M NaCl | 17 | 10 | 90 | 99 | 117 | 105 |
| 0.8M NaCl | 7 | 47 | 118 | 110 | 116 | 132 |
| 1.0M NaCl | 0 | 80 | 134 | 119 | 119 | 128 |
| 1.2M NaCl | 10 | 111 | 118 | 111 | 106 | 121 |
| 1.4M NaCl | 31 | 93 | 135 | 113 | 131 | 155 |
| 1.6M NaCl | 61 | 111 | 108 | 116 | 107 | 136 |
| 1.8M NaCl | 68 | 106 | 107 | 111 | 111 | 135 |

FIG. 6D

| | Total IL12 (ng/mL) | | | | | |
|---|---|---|---|---|---|---|
| | pH 6.0 | pH 6.5 | pH 7.0 | pH 7.5 | pH 8.0 | pH 8.5 |
| 0.4M NaCl | 5 | 4 | 5 | 5 | 7 | 9 |
| 0.6M NaCl | 5 | 3 | 7 | 7 | 7 | 7 |
| 0.8M NaCl | 6 | 8 | 12 | 13 | 12 | 15 |
| 1.0M NaCl | 8 | 14 | 21 | 15 | 22 | 18 |
| 1.2M NaCl | 13 | 19 | 23 | 20 | 23 | 21 |
| 1.4M NaCl | 16 | 20 | 24 | 16 | 19 | 22 |
| 1.6M NaCl | 23 | 25 | 25 | 22 | 21 | 23 |
| 1.8M NaCl | 29 | 27 | 20 | 30 | 29 | 28 |

HIGH-THROUGHPUT CHROMATOGRAPHY SCREENING FOR EXTRACELLULAR VESICLES

CROSS-REFERENCE TO RELATED APPLICATIONS

This PCT application claims the priority benefit of U.S. Provisional Application No. 62/931,089, filed Nov. 5, 2019, which is incorporated herein by reference in its entirety.

FIELD OF DISCLOSURE

The present disclosure relates to high-throughput screening methods for identifying chromatography operational parameters (e.g., binding parameters) and/or reagents for chromatography, such as those that can be used to analyze and/or purify extracellular vesicles (e.g., exosomes) from a sample.

BACKGROUND OF DISCLOSURE

Extracellular vesicles (EVs) (e.g., exosomes) are important mediators of intercellular communication. They are produced by nearly every eukaryotic cell and comprise a membrane and an internal space (i.e., lumen), which is enclosed by the membrane. Depending on the cells from which they are produced, EVs can comprise different lipids, proteins, carbohydrates, and/or nucleic acids. As drug delivery vehicles, EVs (e.g., exosomes) offer many advantages over traditional drug delivery methods as a new treatment modality in many therapeutic areas. However, the ability to purify EVs (e.g., exosomes) on a commercial scale is an important challenge to their development for therapeutic and diagnostic purposes. The currently available technology available for purifying EVs (e.g., exosomes) are time consuming and generally require unit operations such as gradient ultracentrifugation that do not have a clear path to scalability in manufacturing. Therefore, there remains a need for methods that can provide for more rapid and efficient means of purifying EVs (e.g., exosomes) from a sample.

SUMMARY OF DISCLOSURE

Provided herein is a method of purifying an extracellular vesicle (EV) from a sample to improve an EV yield, improve EV ligand density, and/or reduce impurity recovery comprising: (i) contacting the sample to a chromatography resin or medium under a plurality of chromatography operational parameters (e.g., binding parameters), (ii) collecting a fraction comprising the EV from (i), and (iii) determining an EV yield, impurity recovery, and/or EV ligand density from (ii).

Also provided herein is a method of identifying one or more chromatography operational parameters (e.g., binding parameters) for a chromatography for purifying an extracellular vesicle (EV) from a sample comprising the EV and an impurity, the method comprising: (i) contacting the sample to a chromatography resin or medium under a plurality of chromatography operational parameters (e.g., binding parameters), (ii) collecting a fraction comprising the EV from (i), and (iii) determining an EV yield, impurity recovery, and/or EV ligand density from (ii).

Present disclosure further provides a method of screening one or more chromatography reagents for purifying an extracellular vesicle (EV) from a sample comprising the EV and an impurity, the method comprising: (i) contacting the sample to the one or more chromatography reagents under a plurality of chromatography operational parameters (e.g., binding parameters); (ii) collecting a fraction comprising the EV from (i); and (iii) determining an EV yield, impurity recovery, and/or EV ligand density from (ii).

In some aspects, the contacting of the sample to the chromatography resin or medium occurs in an agitated microplate or in miniature columns. In certain aspects, the contacting of the sample to the one or more chromatography reagents occurs in an agitated microplate or in miniature columns. In some aspects, the contacting of the sample is performed in parallel with multiple samples, aliquots of chromatography column, or miniature columns. In some aspects, the miniature column is formally qualified as a scale-down model suitable to produce results appropriate for inclusion in process validation and in therapeutics applications to regulatory agencies.

In some aspects, the methods disclosed herein further comprise (iv) adjusting at least one of the plurality of chromatography operational parameters (e.g., binding parameters) and repeating steps (i) to (iii). In certain aspects, the methods further comprise repeating the adjusting step of (iv) and steps (i) to (iii) until the desired level of EV yield, EV ligand density, and/or impurity recovery is obtained.

In some aspects, the chromatography operational parameters (e.g., binding parameters) comprise a plurality of pHs, a plurality of weak acids and/or conjugate bases, a plurality of alcohols, a plurality of carbohydrates, a plurality of detergents, a plurality of chaotropic agents, a plurality of kosmotropic agents, a plurality of mass challenge, a plurality of residence time, a plurality of temperatures, a plurality of salt concentrations, a plurality of buffers, or any combination thereof. In certain aspects, the chromatography operational parameters (e.g., binding parameters) comprise a plurality of pHs and/or a plurality of salt concentrations.

In some aspects, the chromatography operational parameters (e.g., binding parameters) comprise a plurality of pHs. In certain aspects, the plurality of pHs is between 0 and 14. In some aspects, the plurality of pHs is about 3, about 4, about 5, about 6, about 7, about 8, about 9, about 10, about 11, about 12, or about 13.

In some aspects, the chromatography operational parameters (e.g., binding parameters) comprise a plurality of salt concentrations. In certain aspects, the plurality of salt concentrations is between about 0 M and about 4 M. In some aspects, the salt comprises sodium salt, potassium salt, ammonium salt, calcium salt, magnesium salt, or any combination thereof.

In some aspects, the collecting of the fraction in step (ii) of the methods disclosed herein is performed under a flow through mode, bind and elute mode, or weak-partitioning mode. In certain aspects, the collecting is performed under a weak-partitioning mode.

In some aspects, the methods disclosed herein further comprise measuring the EV using a fluorescence spectroscopy.

In some aspects, the EV yield is determined by comparing a EV particle count of the fraction in (ii) to that of the sample prior to step (a). In some aspects, the EV yield is determined by comparing a light scattering emission signal of the fraction in (ii) to a light scattering emission signal of the sample prior to step (a).

In some aspects, the EV yield is determined by measuring absorbance. In some aspects, the EV yield is determined by measuring light scattering. In some aspects, the EV yield is determined by measuring static light scattering. In some aspects, the EV yield is determined by measuring dynamic light scattering. In some aspects, the EV yield is determined by measuring static turbidity. In some aspects, the EV yield is determined by measuring static light obscuration. In some aspects, the EV yield is determined by measuring static refractive index.

In certain aspects, the light scattering emission signal is generated using an excitation wavelength ranging from about 280 nm to 700 nm and is detected by measuring an emission wavelength that is 0-20 nm longer or shorter than the excitation wavelength and ranging from 260 nm to 720 nm. In some aspects, the EV yield is determined by comparing the absorbance from about 200 nm to 1100 nm of the fraction in (ii) to that of the sample prior to step (a). In some aspects, the absorbance is at about 260 nm, about 280 nm, about 320 nm, about 405 nm, or about 600 nm. In further aspects, the EV yield is determined by comparing a total integrated SEC-HPLC area of intrinsic EV fluorescence at ex460 nm/em470 nm of the fraction in (ii) to that of the sample prior to step (a).

In some aspects, the impurity recovery is determined using an assay comprising an ELISA or Alphalisa. In certain aspects, the ELISA or Alphalisa is capable of measuring an exosome property selected from an amount of exosomes, amount of ligand, or ligand density on the exosomes. In some aspects, the methods disclosed herein additionally comprise calculating selectivity ($\alpha$) by comparing the partition coefficient (Kp) of impurity to the partition coefficient (Kp) of EV in the collected fraction.

In some aspects, a chromatography that can be used with the present methods comprises a size exclusion chromatography, affinity chromatography, ion-exchange chromatography, mixed-mode chromatography, reversed-phase chromatography, hydrophobic interaction chromatography, hydroxyapatite chromatography, immobilized metal affinity chromatography, or any combination thereof. In certain aspects, the chromatography is size exclusion chromatography. In some aspects, the chromatography is ion-exchange chromatography. In certain aspects, the ion-exchange chromatography is a strong cation exchange chromatography. In certain aspects, the chromatography resin or chromatography reagent comprises Poros XS, Hypercell CMM, or CaptoCore700.

In some aspects, a sample comprising the EV is derived from a cell culture. In certain aspects, the cell culture comprises mammalian cells. In some aspects, the mammalian cells comprise human embryonic kidney cells, mesenchymal stem cells, or neuronal cells. In some aspects, the human embryonic kidney cells comprise HEK293 cells. In some aspects, a sample comprising the EV is derived from a body fluid of a subject.

In some aspects, the EV comprises an exosome.

In some aspects, the EV comprises an exogenous biologically active molecule. In certain aspects, the exogenous biologically active molecule comprises a payload and/or a targeting moiety. In some aspects, the payload comprises a therapeutic molecule, adjuvant, immune modulator, or combinations thereof. In certain aspects, the targeting moiety is specific to an organ, tissue, cell, or any combination thereof.

In some aspects, the EV can also comprise a scaffold moiety. In certain aspects, the scaffold moiety comprises Scaffold X. In some aspects, the scaffold moiety comprises Scaffold Y. In certain aspects, the Scaffold X comprises prostaglandin F2 receptor negative regulator (the PTGFRN protein), basigin (the BSG protein), immunoglobulin superfamily member 2 (the IGSF2 protein), immunoglobulin superfamily member 3 (the IGSF3 protein), immunoglobulin superfamily member 8 (the IGSF8 protein), integrin beta-1 (the ITGB1 protein), integrin alpha-4 (the ITGA4 protein), 4F2 cell-surface antigen heavy chain (the SLC3A2 protein), a class of ATP transporter proteins (the ATP1A1, ATP1A2, ATP1A3, ATP1A4, ATP1B3, ATP2B1, ATP2B2, ATP2B3, ATP2B4 proteins), aminopeptidase N (ANPEP; CD13), neprilysin (membrane metalloendopeptidase; MME), ectonucleotide pyrophosphatase/phosphodiesterase family member 1 (ENPP1), neuropilin-1 (NRP1), CD9, CD63, CD81, PDGFR, GPI anchor proteins, lactadherin (MFGE8), LAMP2, LAMP2B, or any combination thereof. In certain aspects, the Scaffold Y comprises myristoylated alanine rich Protein Kinase C substrate (the MARCKS protein); myristoylated alanine rich Protein Kinase C substrate like 1 (the MARCKSL1 protein); brain acid soluble protein 1 (the BASP1 protein), or any combination thereof.

In some aspects, the exogenous biologically active molecules expressed on an EV (e.g., exosome) disclosed herein is linked to the EV via the scaffold moiety. In certain aspects, the exogenous biologically active molecule is linked to the scaffold moiety via a linker. In some aspects, the linker is a polypeptide. In other aspects, the linker is a non-polypeptide moiety.

In some aspects, the methods disclosed herein results in EV yield that is greater than about 5%, greater than about 10%, greater than about 20%, greater than about 30%, greater than about 40%, greater than about 50%, greater than about 60%, greater than about 70%, greater than about 80%, greater than about 90% or more. In certain aspects, the methods disclosed herein results in impurity recovery that is less than about 50%, less than about 40%, less than about 30%, less than about 20%, less than about 10%, less than about 9%, less than about 8%, less than about 7%, less than about 6%, less than about 5%, less than about 4%, less than about 3%, less than about 2%, or less than about 1%. In further aspects, the methods disclosed herein results in EV ligand density that is at least about 5 ligands/EV, at least about 10 ligands/EV, at least about $10^2$ ligands/EV, at least about $10^3$ ligands/EV, at least about $10^4$ ligands/EV, at least about $10^5$ ligands/EV, or at least about $10^6$ ligands/EV.

In some aspects, the one or more binding parameters and/or the one or more chromatography reagents identified using the methods disclosed herein are optimal for purifying the EV from a sample if the EV yield is increased, the impurity recovery is reduced, and/or the EV ligand density is increased compared to the corresponding values in the sample prior to step (a).

Provided herein is a method of purifying an extracellular vesicle (EV) from a sample, the method comprising purifying the EV from the sample with a chromatography using the one or more optimal binding parameters and/or the one or more optimal chromatography reagents identified using the high-throughput methods disclosed herein.

Provided herein is a method of increasing a ligand density of an EV present in a sample, the method comprising contacting the sample to a chromatography resin or medium under the one or more optimal binding parameters and/or the one or more optimal chromatography reagents identified using the high-throughput methods disclosed herein, wherein the optimal binding parameters and/or chromatography reagents increases the ligand density of the EV. In certain aspects, the ligand density is increased by at least about 5%, at least about 10%, at least about 20%, at least about 30%, at least about 40%, at least about 50%, at least about 60%, at least about 70%, at least about 80%, at least about 90%, at least about 100%, at least about 200%, at least about 300%, at least about 400%, or at least about 500% or more compared to a reference (e.g., ligand density of a corresponding EV under different binding parameters and/or chromatography reagents or the ligand density of the EV in the sample prior to the contacting).

Present disclosure further provides a method of decreasing an amount of impurity in a sample comprising an EV, the method comprising contacting the sample to a chromatography resin or medium under the one or more optimal binding parameters and/or the one or more optimal chromatography reagents identified using the high-throughput methods disclosed herein, wherein the optimal binding parameters and/or chromatography reagents decreases the amount of impurity in the sample. In certain aspects, the amount of impurity is decreased by at least about %, at least about 10%, at least about 20%, at least about 30%, at least about 40%, at least about 50%, at least about 60%, at least about 70%, at least about 80%, at least about 90% or more compared to a reference (e.g., amount of impurity present in a sample using different binding parameters and/or chromatography reagents or the amount of impurity present in the sample prior to the contacting).

Also provided herein is a method of increasing an EV yield in a sample, the method comprising contacting the sample to a chromatography resin or medium under the one or more optimal binding parameters and/or the one or more optimal chromatography reagents identified using the high-throughput methods disclosed herein, wherein optimal binding parameters and/or chromatography reagents increases the EV yield of the sample. In certain aspects, the EV yield is increased by at least about 5%, at least about 10%, at least about 20%, at least about 30%, at least about 40%, at least about 50%, at least about 60%, at least about 70%, at least about 80%, at least about 90%, at least about 100% or more compared to a reference (e.g., EV yield of a sample under different binding parameters and/or chromatography reagents or the EV yield of the sample prior to the contacting).

BRIEF DESCRIPTION OF FIGURES

In FIG. 3A, the results of an initial screening of 48 different chromatography resins are provided. Specifically, the relationship between EV yield ("particle recovery") (x-axis) and impurity recovery (y-axis) are provided for the different resins. FIG. 3B provides a comparison of EV-specific signal (top row) and impurity recovery (bottom row) for four lead resins identified in FIG. 3A (i.e., resins 33, 38, 40, and 41). The star represents a suitable operational condition for a platform process involving the binding parameters tested.

FIGS. 5A and 5B provide the effect of different wash buffer conditions on the selective desorption of DNA impurity from a sample using anion-exchange (AEX) chromatography. FIG. 5A provides a table showing the different wash buffer conditions tested (40 total). AEX eluate residual DNA was assessed using the Quant-iT PicoGreen DNA assay; and exosome yield was estimated using UV280 nm absorbance. FIG. 5B shows the relationship between residual DNA recovered (as shown as PicoGreen raw intensity units) and the amount of exosomes recovered (as shown as absorbance). The dotted circle represents conditions with desired properties (i.e., low impurity and high exosome recovery).

FIGS. 6A, 6B, 6C, and 6D provide the results from a high-throughput screen of a flowthrough mixed-mode resin application for removal of a proteoglycan impurity from an engineered exosome. Exosome recovery was determined by UV280 nm and intrinsic fluorescence using SE-HPLC (FIGS. 6A and 6B). The recovery of an exosome specific ligand was measured using a ligand-specific Alphalisa (FIG. 6D). Exosome and ligand recovery was compared to proteoglycan impurity removal (FIG. 6C) as a means to evaluate resin selectivity across the characterization space.

DETAILED DESCRIPTION OF DISCLOSURE

Figure 1:
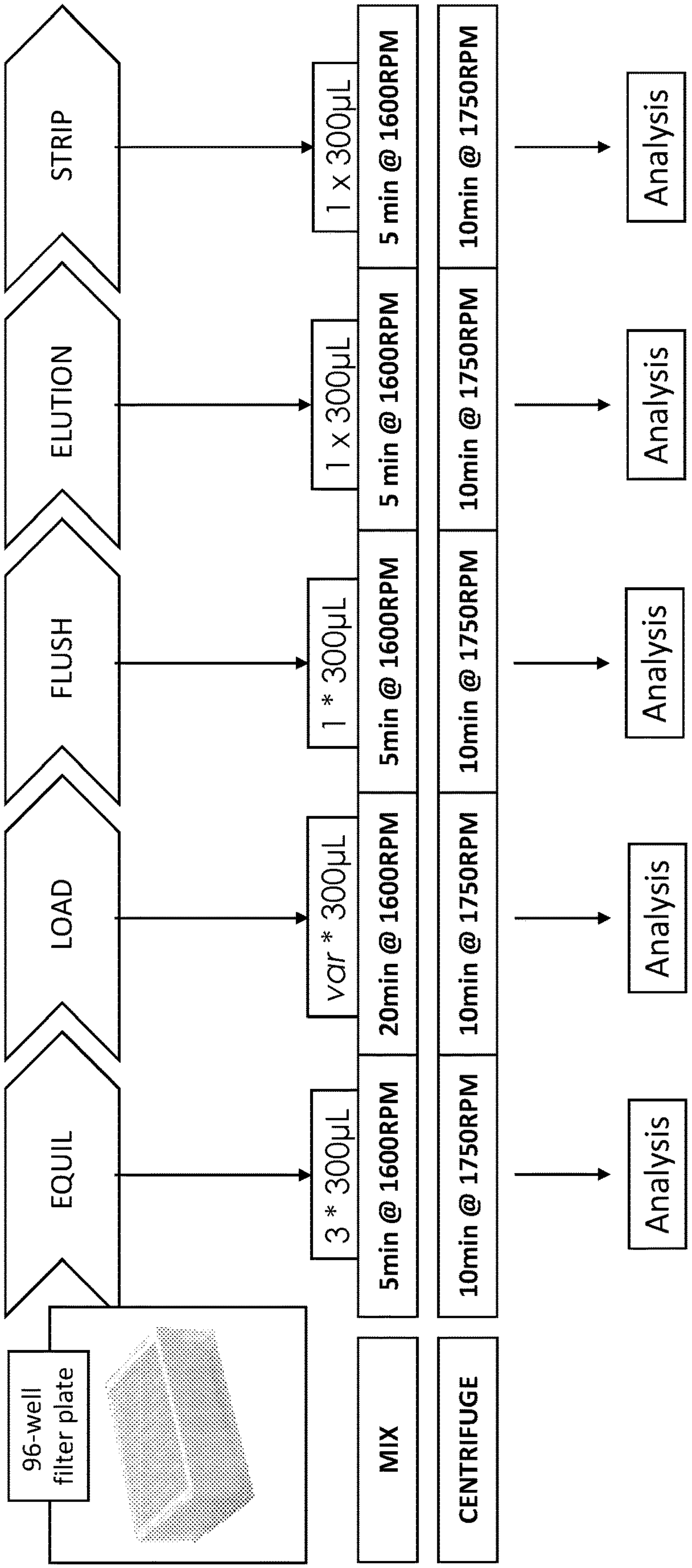
FIG. 1 provides a schematic of an exemplary high-throughput screening method of identifying one or more chromatography operational parameters for a chromatography described herein.

The present disclosure is directed to high-throughput screening methods for identifying one or more thermodynamic (e.g. partition coefficient, characteristic charge, maximum capacity), mass transfer (e.g. uptake, resident time, breakthrough curves), or physical parameters (e.g., temperature, volume needed for elution, resin type, pH) (collectively referred to herein as "chromatography operational parameters") and/or reagents for chromatography. The aforementioned parameters can also be identified for impurities and/or exosomes using this methodology. In some aspects, one or more chromatography operational parameters and/or reagents are useful for purifying EVs (e.g., exosomes) from a sample using chromatography. In certain aspects, the methods disclosed herein can be used to develop impurity removal strategies, such as selective washes, or to optimize an elution.

I. Definitions

In order that the present description can be more readily understood, certain terms are first defined. Additional definitions are set forth throughout the detailed description.

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, nucleotide sequences are written left to right in 5' to 3' orientation. Amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower).

As used herein, the term "high-throughput" refers to the process of assaying a large number of variables (e.g., samples, parameters, or reagents) in a relatively short period of time. The high-throughput screening methods disclosed herein can be performed using various assays known in the art. In certain aspects, a high-throughput method disclosed herein is performed using a 96-well plate or miniature packed column such as a ROBOCOLUMN™. Miniature packed columns afford evaluation of multiple chromatographic plates/stages and because it incorporates mass transfer and other effects on chromatographic resolution, thereby provides a more representative scale-down model.

As described herein, a high-throughput method disclosed herein can be used to screen a plurality of chromatography operational parameters (e.g., thermodynamic, mass transfer, and/or physical parameters) that are suitable for one or more steps of a chromatography process (e.g., a binding, wash, and/or elution step) and/or chromatography reagents in less time than a traditional screening experiment conducted at lab-scale where chromatographic runs are typically performed sequentially. In some aspects, the methods disclosed herein comprises running in parallel multiple screening processes (e.g., multiple samples, multiple aliquots of chromatography column or miniature columns). Not to be bound by any one theory, the ability to run multiple screening processes in parallel can greatly decrease the screening time. As used herein, a chromatography operational parameter that is suitable for the binding step of a chromatography is referred to as a "binding parameter." As used herein, a chromatography operational parameter that is suitable for the washing step of a chromatography is referred to as a "washing parameter." In some aspects, a chromatography operational parameter that is suitable for the elution step of a chromatography is referred to as a "elution parameter." In some aspects, a high-throughput method disclosed herein can screen a plurality of chromatography operational parameters (e.g., binding parameters) and/or chromatography reagents (e.g., those described herein) in less than about a week, less than about six days, less than about five days, less than about four days, less than about three days, less than about two days, less than about one day, less than about twelve hours, less than about six hours, less than about three hours, less than about one hour, less than about thirty minutes, less than about ten minutes, or less than about five minutes.

As used herein, the term "chromatography" refers to process by which a molecule of interest (e.g., EVs, e.g., exosomes) in a mixture is separated from other molecules (e.g., impurity) in a mixture as a result of differences in rates at which the individual molecules of the mixture migrate through a stationary medium under the influence of a moving phase. In certain aspects, chromatography separates a molecule of interest (e.g., EVs, e.g., exosomes) in a mixture from other molecules in the mixture (e.g., impurity) by percolation of the mixture through a resin or membrane, which adsorbs or retains, under particular binding conditions, a particular molecule more or less strongly due to one or more properties of the molecule, such as isoelectric point, hydrophobicity, size, and structure. Non-limiting examples of chromatography that can be used with the present disclosure include a size exclusion chromatography, affinity chromatography, ion-exchange chromatography, mixed-mode chromatography, hydrophobic interaction chromatography, hydroxyapatite chromatography, immobilized metal affinity chromatography, or any combination thereof.

As used herein, the terms "impurity" and "contaminant" are interchangeable and refer to any molecule other than the EV (e.g., exosome) present in a sample. Non-limiting examples of impurity include protein variants, such as aggregated proteins, high molecular weight species, low molecular weight species and fragments, and deamidated species; other proteins from host cells that secrete the protein being purified (host cell proteins); proteins that are part of an absorbent used for affinity chromatography that can leach into a sample during prior purification steps, such as Protein A; endotoxins; and viruses.

The terms “intrinsic fluorescence,” “autofluorescence,” and “auto-fluorescence” refer to the natural emission of light by biological structures after they have absorbed light, and is distinguished from light emitted by artificial fluorescent markers, dyes, or fluorophores (referred to herein as “extrinsic fluorescence”). In some aspects, the detector can be a fluorescence detector. In some aspects, the detector can be a multi-wavelength detector.

As used herein, the term “absorbance” refers to the capacity of a substance (e.g., biological structures, e.g., exosomes) to absorb light of a specified wavelength and is measured as the $\log_{10}$ ratio of incident light to transmitted light. Absorbance can be caused by, e.g., absorption, scattering, reflection, or other phenomena. In some aspects, the detector for absorbance can be a optical density detector. In some aspects, the detector for absorbance and be a luminiscence detector. In some aspect, the detector for absorbance can be a visual light detector. In some aspects, the detector for absorbance can be a ultraviolet detector.

As used herein, the term “light scattering” refers to scattering and/or reflection of a light source from a focal beam. In some embodiments, the light scattering can be detected at a single angle from the source (e.g., 90 degrees), or can be detected at multiple angles (e.g., in the case of multi-angle light scattering). In some embodiments, the light source is a laser. In some embodiments, the light source is at a wavelength in the ultraviolet spectrum, the visual spectrum, the infrared spectrum, or combinations thereof. In some embodiments, the light scattering is elastic. In some embodiments the light scattering is inelastic. In some preferred embodiments, the light scattering is Rayleigh (elastic) light scattering.

As used herein, the terms “excitation wavelength” and “absorbance wavelength” are interchangeable and refer to a wavelength of a light source used to excite the samples. The wavelengths of a light source are controlled by appropriate filters to block or pass specific wavelengths. The excitation wavelength corresponds inversely to the radiation energy of the light source, i.e., longer excitation wavelengths indicate lower radiation energy, while shorter excitation wavelengths indicate higher radiation energy.

As used herein, the term “emission wavelength” refers to the wavelength of a signal emitted, which is then detected by a detector. Emission signals can be emitted as a result of light scattering after nanoparticles are excited by a light source. In some aspects, the light scattering is inelastic. In some aspects, the light scattering is Rayleigh (elastic) light scattering. In some aspects, the light source can be fluorescence, and the emission wavelength is a wavelength of fluorescence. In some aspects, the fluorescence is intrinsic fluorescence.

As used herein, the term “extracellular vesicle” or “EV” refers to a cell-derived vesicle comprising a membrane that encloses an internal space. Extracellular vesicles comprise all membrane-bound vesicles (e.g., exosomes, nanovesicles) that have a smaller diameter than the cell from which they are derived. In some aspects, extracellular vesicles range in diameter from 20 nm to 1000 nm, and can comprise various macromolecular payload either within the internal space (i.e., lumen), displayed on the external surface of the extracellular vesicle, and/or spanning the membrane. In some aspects, the payload can comprise nucleic acids, proteins, carbohydrates, lipids, small molecules, and/or combinations thereof. In some aspects, an EV comprises multiple (e.g., two or more) payloads or other exogenous biologically active molecules. In certain aspects, an extracellular vehicle can further comprise one or more scaffold moieties. By way of example and without limitation, extracellular vesicles include apoptotic bodies, fragments of cells, vesicles derived from cells by direct or indirect manipulation (e.g., by serial extrusion or treatment with alkaline solutions), vesiculated organelles, and vesicles produced by living cells (e.g., by direct plasma membrane budding or fusion of the late endosome with the plasma membrane). Extracellular vesicles can be derived from a living or dead organism, explanted tissues or organs, prokaryotic or eukaryotic cells, and/or cultured cells. In some aspects, the extracellular vesicles are produced by cells that express one or more transgene products. The EVs disclosed herein have been modified and therefore, do not comprise naturally occurring EVs.

As used herein, the term “exosome” refers to an extracellular vesicle with a diameter between 20-300 nm (e.g., between 40-200 nm). Exosomes comprise a membrane that encloses an internal space (i.e., lumen), and, in some aspects, can be generated from a cell (e.g., producer cell) by direct plasma membrane budding or by fusion of the late endosome with the plasma membrane. In some aspects, an exosome comprises multiple (e.g., two or more) exogenous biologically active molecules (e.g., as described herein). In certain aspects, an exosome further comprises one or more scaffold moieties. As described infra, exosomes can be derived from a producer cell, and isolated from the producer cell based on its size, density, biochemical parameters, or a combination thereof. In some aspects, the EVs (e.g., exosomes) of the present disclosure are produced by cells that express one or more transgene products. The exosomes of the present disclosure are modified and therefore, do not comprise naturally occurring exosomes.

As used herein, the term “nanovesicle” refers to an extracellular vesicle with a diameter between 20-250 nm (e.g., between 30-150 nm) and is generated from a cell (e.g., producer cell) by direct or indirect manipulation such that the nanovesicle would not be produced by the cell without the manipulation. Appropriate manipulations of the cell to produce the nanovesicles include but are not limited to serial extrusion, treatment with alkaline solutions, sonication, or combinations thereof. In some aspects, production of nanovesicles can result in the destruction of the producer cell. In some aspects, population of nanovesicles described herein are substantially free of vesicles that are derived from cells by way of direct budding from the plasma membrane or fusion of the late endosome with the plasma membrane. In some aspects, a nanovesicle comprises multiple (e.g., at least two) exogenous biologically active molecules. In certain aspects, a nanovesicle further comprises one or more scaffold moieties. Nanovesicles, once derived from a producer cell, can be isolated from the producer cell based on its size, density, biochemical parameters, or a combination thereof. As used herein, nanovesicles have been modified and therefore, do not comprise naturally occurring nanovesicles.

As used herein the term “surface-engineered” EVs, e.g., exosomes (e.g., Scaffold X-engineered EVs, e.g., exosomes) refers to an EV (e.g., exosome) with the membrane or the surface modified in its composition, so that the membrane or the surface of the engineered EV (e.g., exosome), is different from either that of the EV prior to the modification or of the naturally occurring EV. The engineering can be on the surface of the EV (e.g., exosome) or in the membrane of the EV (e.g., exosome) so that the surface of the EV, e.g., exosome, is changed. For example, the membrane is modified in its composition of a protein, a lipid, a small molecule, a carbohydrate, etc. The composition can be changed by a chemical, a physical, or a biological method or by being produced from a cell previously or concurrently modified by a chemical, a physical, or a biological method. Specifically, the composition can be changed by a genetic engineering or by being produced from a cell previously modified by genetic engineering. In some aspects, a surface-engineered EV, e.g., exosome, comprises multiple (e.g., at least two) exogenous biologically active molecules. In certain aspects, the exogenous biologically active molecules can comprise an exogenous protein (i.e., a protein that the EV, e.g., exosome, does not naturally express) or a fragment or variant thereof that can be exposed to the surface of the EV, e.g., exosome, or can be an anchoring point (attachment) for a moiety exposed on the surface of the EV, e.g., exosome. In other aspects, a surface-engineered EV, e.g., exosome, comprises a higher expression (e.g., higher number) of a natural exosome protein (e.g., Scaffold X) or a fragment or variant thereof that can be exposed to the surface of the EV, e.g., exosome, or can be an anchoring point (attachment) for a moiety exposed on the surface of the EV, e.g., exosome.

As used herein the term "lumen-engineered" EV (e.g., exosome) (e.g., Scaffold Y-engineered exosome) refers to an EV, e.g., exosome, with the membrane or the lumen of the EV, e.g., exosome, modified in its composition so that the lumen of the engineered EV, e.g., exosome, is different from that of the EV, e.g., exosome, prior to the modification or of the naturally occurring EV, e.g., exosome. The engineering can be directly in the lumen or in the membrane of the EV, e.g., exosome so that the lumen of the EV, e.g., exosome is changed. For example, the membrane is modified in its composition of a protein, a lipid, a small molecule, a carbohydrate, etc. so that the lumen of the EV, e.g., exosome is modified. The composition can be changed by a chemical, a physical, or a biological method or by being produced from a cell previously modified by a chemical, a physical, or a biological method. Specifically, the composition can be changed by a genetic engineering or by being produced from a cell previously modified by genetic engineering. In some aspects, a lumen-engineered exosome comprises multiple (e.g., at least two) exogenous biologically active molecules. In certain aspects, the exogenous biologically active molecules can comprise an exogenous protein (i.e., a protein that the EV, e.g., exosome does not naturally express) or a fragment or variant thereof that can be exposed in the lumen of the EV, e.g., exosome or can be an anchoring point (attachment) for a moiety exposed on the inner layer of the EV, e.g., exosome. In other aspects, a lumen-engineered EV, e.g., exosome, comprises a higher expression of a natural exosome protein (e.g., Scaffold X or Scaffold Y) or a fragment or variant thereof that can be exposed to the lumen of the exosome or can be an anchoring point (attachment) for a moiety exposed in the lumen of the exosome.

The term "modified," when used in the context of EVs, e.g., exosomes described herein, refers to an alteration or engineering of an EV, e.g., exosome and/or its producer cell, such that the modified EV, e.g., exosome is different from a naturally-occurring EV, e.g., exosome. In some aspects, a modified EV, e.g., exosome described herein comprises a membrane that differs in composition of a protein, a lipid, a small molecular, a carbohydrate, etc. compared to the membrane of a naturally-occurring EV, e.g., exosome (e.g., membrane comprises higher density or number of natural exosome proteins and/or membrane comprises multiple (e.g., at least two) biologically active molecules that are not naturally found in exosomes (e.g., therapeutic molecules (e.g., antigen), targeting moiety, adjuvant, and/or immune modulator). As used herein, biologically active molecules that are not naturally found in exosomes are also described as "exogenous biologically active molecules.". In certain aspects, such modifications to the membrane changes the exterior surface of the EV, e.g., exosome (e.g., surface-engineered EVs, e.g., exosomes described herein). In certain aspects, such modifications to the membrane changes the lumen of the EV, e.g., exosome (e.g., lumen-engineered EVs, e.g., exosomes described herein).

As used herein, the term "scaffold moiety" refers to a molecule that can be used to anchor a payload or any other exogenous biologically active molecule of interest (e.g., therapeutic molecule (e.g., antigen), targeting moiety, adjuvant, and/or immune modulator) to the EV, e.g., exosome, either on the luminal surface or on the exterior surface of the EV, e.g., exosome. In certain aspects, a scaffold moiety comprises a synthetic molecule. In some aspects, a scaffold moiety comprises a non-polypeptide moiety. In other aspects, a scaffold moiety comprises a lipid, carbohydrate, or protein that naturally exists in the EV, e.g., exosome. In some aspects, a scaffold moiety comprises a lipid, carbohydrate, or protein that does not naturally exist in the EV, e.g., exosome. In certain aspects, a scaffold moiety is Scaffold X. In some aspects, a scaffold moiety is Scaffold Y. In further aspects, a scaffold moiety comprises both Scaffold X and Scaffold Y. Non-limiting examples of other scaffold moieties that can be used with the present disclosure include: aminopeptidase N (CD13); Neprilysin, AKA membrane metalloendopeptidase (MME); ectonucleotide pyrophosphatase/phosphodiesterase family member 1 (ENPP1); Neuropilin-1 (NRP1); CD9, CD63, CD81, PDGFR, GPI anchor proteins, lactadherin, LAMP2, and LAMP2B.

As used herein, the term "Scaffold X" refers to exosome proteins that have recently been identified on the surface of exosomes. See, e.g., U.S. Pat. No. 10,195,290, which is incorporated herein by reference in its entirety. Non-limiting examples of Scaffold X proteins include: prostaglandin F2 receptor negative regulator ("the PTGFRN protein"); basigin ("the BSG protein"); immunoglobulin superfamily member 2 ("the IGSF2 protein"); immunoglobulin superfamily member 3 ("the IGSF3 protein"); immunoglobulin superfamily member 8 ("the IGSF8 protein"); integrin beta-1 ("the ITGB1 protein"); integrin alpha-4 ("the ITGA4 protein"); 4F2 cell-surface antigen heavy chain ("the SLC3A2 protein"); and a class of ATP transporter proteins ("the ATP1A1 protein," "the ATP1A2 protein," "the ATP1A3 protein," "the ATP1A4 protein," "the ATP1B3 protein," "the ATP2B1 protein," "the ATP2B2 protein," "the ATP2B3 protein," "the ATP2B protein"). In some aspects, a Scaffold X protein can be a whole protein or a fragment thereof (e.g., functional fragment, e.g., the smallest fragment that is capable of anchoring another moiety on the exterior surface or on the luminal surface of the EV, e.g., exosome). In some aspects, a Scaffold X can anchor a moiety (e.g., antigen, adjuvant, and/or immune modulator) to the external surface or the luminal surface of the exosome.

As used herein, the term "Scaffold Y" refers to exosome proteins that were newly identified within the lumen of exosomes. See, e.g., International Appl. No. PCT/US2018/061679, which is incorporated herein by reference in its entirety. Non-limiting examples of Scaffold Y proteins include: myristoylated alanine rich Protein Kinase C substrate ("the MARCKS protein"); myristoylated alanine rich Protein Kinase C substrate like 1 ("the MARCKSL1 protein"); and brain acid soluble protein 1 ("the BASP1 protein"). In some aspects, a Scaffold Y protein can be a whole protein or a fragment thereof (e.g., functional fragment, e.g., the smallest fragment that is capable of anchoring a moiety to the luminal surface of the exosome). In some aspects, a Scaffold Y can anchor a moiety (e.g., antigen, adjuvant, and/or immune modulator) to the luminal surface of the EV, e.g., exosome.

As used herein, the term "fragment" of a protein (e.g., therapeutic protein, Scaffold X, or Scaffold Y) refers to an amino acid sequence of a protein that is shorter than the naturally-occurring sequence, N- and/or C-terminally deleted or any part of the protein deleted in comparison to the naturally occurring protein. As used herein, the term "functional fragment" refers to a protein fragment that retains protein function. Accordingly, in some aspects, a functional fragment of a Scaffold X protein retains the ability to anchor a moiety on the luminal surface or on the exterior surface of the EV, e.g., exosome. Similarly, in certain aspects, a functional fragment of a Scaffold Y protein retains the ability to anchor a moiety on the luminal surface of the EV, e.g., exosome. Whether a fragment is a functional fragment can be assessed by any art known methods to determine the protein content of EVs, e.g., exosomes including Western Blots, FACS analysis and fusions of the fragments with autofluorescent proteins like, e.g., GFP. In certain aspects, a functional fragment of a Scaffold X protein retains at least about 50%, at least about 60%, at least about 70%, at least about 80%, at least about 90% or at least about 100% of the ability, e.g., an ability to anchor a moiety, of the naturally occurring Scaffold X protein. In some aspects, a functional fragment of a Scaffold Y protein retains at least about 50%, at least about 60%, at least about 70%, at least about 80%, at least about 90% or at least about 100% of the ability, e.g., an ability to anchor another molecule, of the naturally occurring Scaffold Y protein.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another aspect, a string of amino acids can be conservatively replaced with a structurally similar string that differs in order and/or composition of side chain family members.

The term "percent sequence identity" or "percent identity" between two polynucleotide or polypeptide sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence.

The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences may be accomplished using readily available software both for online use and for download. Suitable software programs are available from various sources, and for alignment of both protein and nucleotide sequences. One suitable program to determine percent sequence identity is bl2seq, part of the BLAST suite of programs available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at worldwideweb.ebi.ac.uk/Tools/psa.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

One skilled in the art will appreciate that the generation of a sequence alignment for the calculation of a percent sequence identity is not limited to binary sequence-sequence comparisons exclusively driven by primary sequence data. Sequence alignments can be derived from multiple sequence alignments. One suitable program to generate multiple sequence alignments is ClustalW2, available from worldwideweb.clustal.org. Another suitable program is MUSCLE, available from worldwideweb.drive5.com/muscle/. ClustalW2 and MUSCLE are alternatively available, e.g., from the EBI.

It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at worldwideweb.tcoffee.org, and alternatively available, e.g., from the EBI. It will also be appreciated that the final alignment used to calculate percent sequence identity may be curated either automatically or manually.

The polynucleotide variants can contain alterations in the coding regions, non-coding regions, or both. In one aspect, the polynucleotide variants contain alterations which produce silent substitutions, additions, or deletions, but do not alter the properties or activities of the encoded polypeptide. In another aspect, nucleotide variants are produced by silent substitutions due to the degeneracy of the genetic code. In other aspects, variants in which 5-10, 1-5, or 1-2 amino acids are substituted, deleted, or added in any combination. Polynucleotide variants can be produced for a variety of reasons, e.g., to optimize codon expression for a particular host (change codons in the human mRNA to others, e.g., a bacterial host such as *E. coli*).

Naturally occurring variants are called "allelic variants," and refer to one of several alternate forms of a gene occupying a given locus on a chromosome of an organism (Genes II, Lewin, B., ed., John Wiley & Sons, New York (1985)). These allelic variants can vary at either the polynucleotide and/or polypeptide level and are included in the present disclosure. Alternatively, non-naturally occurring variants can be produced by mutagenesis techniques or by direct synthesis.

Using known methods of protein engineering and recombinant DNA technology, variants can be generated to improve or alter the characteristics of the polypeptides. For instance, one or more amino acids can be deleted from the N-terminus or C-terminus of the secreted protein without substantial loss of biological function. Ron et al., *J. Biol. Chem.* 268: 2984-2988 (1993), incorporated herein by reference in its entirety, reported variant KGF proteins having heparin binding activity even after deleting 3, 8, or 27 amino-terminal amino acid residues. Similarly, interferon gamma exhibited up to ten times higher activity after deleting 8-10 amino acid residues from the carboxy terminus of this protein. (Dobeli et al., *J. Biotechnology* 7:199-216 (1988), incorporated herein by reference in its entirety.)

Moreover, ample evidence demonstrates that variants often retain a biological activity similar to that of the naturally occurring protein. For example, Gayle and coworkers (*J. Biol. Chem* 268:22105-22111 (1993), incorporated herein by reference in its entirety) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See Abstract.) In fact, only 23 unique amino acid sequences, out of more than 3,500 nucleotide sequences examined, produced a protein that significantly differed in activity from wild-type.

As stated above, polypeptide variants include, e.g., modified polypeptides. Modifications include, e.g., acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation (Mei et al., *Blood* 116:270-79 (2010), which is incorporated herein by reference in its entirety), proteolytic processing, phosphorylation, prenylation, racemization, selenoylation, sulfation, transfer-RNA mediated addition of amino acids to proteins such as arginylation, and ubiquitination. In some aspects, Scaffold X and/or Scaffold Y is modified at any convenient location.

As used herein the terms "linked to," "conjugated to," and "anchored to" are used interchangeably and refer to a covalent or non-covalent bond formed between a first moiety and a second moiety, e.g., Scaffold X and an exogenous biologically active molecule, respectively, e.g., a scaffold moiety expressed in or on the extracellular vesicle and an antigen, e.g., Scaffold X (e.g., a PTGFRN protein), respectively, in the luminal surface of or on the external surface of the extracellular vesicle.

The term "encapsulated", or grammatically different forms of the term (e.g., encapsulation, or encapsulating), refers to a status or process of having a first moiety (e.g., exogenous biologically active molecule, e.g., antigen, adjuvant, or immune modulator) inside a second moiety (e.g., an EV, e.g., exosome) without chemically or physically linking the two moieties. In some aspects, the term "encapsulated" can be used interchangeably with "in the lumen of". Non-limiting examples of encapsulating a first moiety (e.g., exogenous biologically active molecule, e.g., antigen, adjuvant, or immune modulator) into a second moiety (e.g., EVs, e.g., exosomes) are disclosed elsewhere herein.

As used herein, the term "producer cell" refers to a cell used for generating an EV, e.g., exosome. A producer cell can be a cell cultured in vitro, or a cell in vivo. A producer cell includes, but not limited to, a cell known to be effective in generating EVs, e.g., exosomes, e.g., HEK293 cells, Chinese hamster ovary (CHO) cells, mesenchymal stem cells (MSCs), BJ human foreskin fibroblast cells, fHDF fibroblast cells, AGE.HN® neuronal precursor cells, CAP® amniocyte cells, adipose mesenchymal stem cells, RPTEC/TERT1 cells. In certain aspects, a producer cell is not an antigen-presenting cell. In some aspects, a producer cell is not a dendritic cell, a B cell, a mast cell, a macrophage, a neutrophil, Kupffer-Browicz cell, cell derived from any of these cells, or any combination thereof.

As used herein, the terms "isolate," "isolated," and "isolating" or "purify," "purified," and "purifying" as well as "extracted" and "extracting" are used interchangeably and refer to the state of a preparation (e.g., a plurality of known or unknown amount and/or concentration) of desired EVs, that have undergone one or more processes of purification, e.g., a selection or an enrichment of the desired EV preparation. In some aspects, isolating or purifying as used herein is the process of removing, partially removing (e.g., a fraction) of the EVs from a sample containing producer cells. In some aspects, an isolated EV composition has no detectable undesired activity or, alternatively, the level or amount of the undesired activity is at or below an acceptable level or amount. In other aspects, an isolated EV composition has an amount and/or concentration of desired EVs at or above an acceptable amount and/or concentration. In other aspects, the isolated EV composition is enriched as compared to the starting material (e.g., producer cell preparations) from which the composition is obtained. This enrichment can be by 10%, 20%, 30%, 40%, 50%, 60%, 70%, 80%, 90%, 95%, 96%, 97%, 98%, 99%, 99.9%, 99.99%, 99.999%, 99.9999%, or greater than 99.9999% as compared to the starting material. In some aspects, isolated EV preparations are substantially free of residual biological products. In some aspects, the isolated EV preparations are 100% free, 99% free, 98% free, 97% free, 96% free, 95% free, 94% free, 93% free, 92% free, 91% free, or 90% free of any contaminating biological matter. Residual biological products can include abiotic materials (including chemicals) or unwanted nucleic acids, proteins, lipids, or metabolites. Substantially free of residual biological products can also mean that the EV composition contains no detectable producer cells and that only EVs are detectable.

As used herein, the term "immune modulator" refers to an agent that acts on a target (e.g., a target cell) that is contacted with the extracellular vesicle, and regulates the immune system. Non-limiting examples of immune modulator that can be introduced into an EV (e.g., exosome) and/or a producer cell include agents such as, modulators of checkpoint inhibitors, ligands of checkpoint inhibitors, cytokines, derivatives thereof, or any combination thereof. The immune modulator can also include an agonist, an antagonist, an antibody, an antigen-binding fragment, a polynucleotide, such as siRNA, miRNA, lncRNA, mRNA, DNA, or a small molecule.

As used herein, the term a "bio-distribution modifying agent" or "targeting moiety" refers to an agent that can modify the distribution of extracellular vesicles (e.g., exosomes, nanovesicles) in vivo or in vitro (e.g., in a mixed culture of cells of different varieties). The bio-distribution agent can be a biological molecule, such as a protein, a peptide, a lipid, or a carbohydrate, or a synthetic molecule. For example, the bio-distribution modifying agent can be an antibody, a synthetic polymer (e.g., PEG), a natural ligand (e.g., albumin), a recombinant protein (e.g., XTEN), but not limited thereto. In certain aspects, the bio-distribution modifying agent is displayed on the surface of EVs. The bio-distribution modifying agent can be displayed on the EV surface by being fused to a scaffold protein (e.g., Scaffold X) (e.g., as a genetically encoded fusion molecule). In some aspects, the bio-distribution modifying agent can be displayed on the EV surface by chemical reaction attaching the bio-distribution modifying agent to an EV surface molecule. A non-limiting example is PEGylation. In some aspects, EVs disclosed herein (e.g., exosomes) can further comprise a bio-distribution modifying agent (in addition to an antigen, adjuvant, or immune modulator). In some aspects, bio-distribution modifying agent (i.e., targeting moiety) described above can be combined with a functional moiety, such as a small molecule (e.g., STING, ASO), a drug, and/or a therapeutic protein.

As used herein, the term "payload" refers to an agent that acts on a target (e.g., a target cell) that is contacted with the EV. Non-limiting examples of payload that can be included on the EV, e.g., exosome, are an antigen, an adjuvant, and/or an immune modulator. Payloads that can be introduced into an EV, e.g., exosome, and/or a producer cell include agents such as, nucleotides (e.g., nucleotides comprising a detectable moiety or a toxin or that disrupt transcription), nucleic acids (e.g., DNA or mRNA molecules that encode a polypeptide such as an enzyme, or RNA molecules that have regulatory function such as miRNA, dsDNA, lncRNA, and siRNA), amino acids (e.g., amino acids comprising a detectable moiety or a toxin or that disrupt translation), polypeptides (e.g., enzymes), lipids, carbohydrates, and small molecules (e.g., small molecule drugs and toxins). In certain aspects, a payload comprises an exogenous biologically active molecule (e.g., those disclosed herein).

As used herein, the term "biologically active molecule" refers to an agent that has activity in a biological system (e.g., a cell or a human subject), including, but not limited to a protein, polypeptide or peptide including, but not limited to, a structural protein, an enzyme, a cytokine (such as an interferon and/or an interleukin) an antibiotic, a polyclonal or monoclonal antibody, or an effective part thereof, such as an Fv fragment, which antibody or part thereof may be natural, synthetic or humanized, a peptide hormone, a receptor, a signaling molecule or other protein; a nucleic acid, as defined below, including, but not limited to, an oligonucleotide or modified oligonucleotide, an anti sense oligonucleotide or modified anti sense oligonucleotide, cDNA, genomic DNA, an artificial or natural chromosome (e.g. a yeast artificial chromosome) or a part thereof, RNA, including mRNA, tRNA, rRNA or a ribozyme, or a peptide nucleic acid (PNA); a virus or virus-like particles; a nucleotide or ribonucleotide or synthetic analogue thereof, which may be modified or unmodified; an amino acid or analogue thereof, which may be modified or unmodified; a non-peptide (e.g., steroid) hormone; a proteoglycan; a lipid; or a carbohydrate. In certain aspects, a biologically active molecule comprises a therapeutic molecule (e.g., an antigen), a targeting moiety (e.g., an antibody or an antigen-binding fragment thereof), an adjuvant, an immune modulator, or any combination thereof. In some aspects, the biologically active molecule comprises a macromolecule (e.g., a protein, an antibody, an enzyme, a peptide, DNA, RNA, or any combination thereof). In some embodiments, the biologically active molecule comprises a small molecule (e.g., an antisense oligomer (ASO), an siRNA, STING, a pharmaceutical drug, or any combination thereof). In some embodiments, the biologically active molecules are exogenous to the exosome, i.e., not naturally found in the exosome.

As used herein, the term "therapeutic molecule" refers to any molecule that can treat and/or prevent a disease or disorder in a subject (e.g., human subject). In some aspects, a therapeutic molecule comprises an antigen. As used herein, the term "antigen" refers to any agent that when introduced into a subject elicits an immune response (cellular or humoral) to itself.

As used herein, the term "antibody" encompasses an immunoglobulin whether natural or partly or wholly synthetically produced, and fragments thereof. The term also covers any protein having a binding domain that is homologous to an immunoglobulin binding domain. "Antibody" further includes a polypeptide comprising a framework region from an immunoglobulin gene or fragments thereof that specifically binds and recognizes an antigen. Use of the term antibody is meant to include whole antibodies, polyclonal, monoclonal and recombinant antibodies, fragments thereof, and further includes single-chain antibodies, humanized antibodies, murine antibodies, chimeric, mouse-human, mouse-primate, primate-human monoclonal antibodies, anti-idiotype antibodies, antibody fragments, such as, e.g., scFv, $(scFv)_2$, Fab, Fab', and $F(ab')_2$, $F(ab\ 1)_2$, Fv, dAb, and Fd fragments, diabodies, and antibody-related polypeptides. Antibody includes bispecific antibodies and multispecific antibodies so long as they exhibit the desired biological activity or function. In some aspects, the antibody or antigen-binding fragment thereof comprises a scFv, scFab, scFab-Fc, nanobody, or any combination thereof. In some aspects, the antibody or antigen-binding fragment thereof comprises an agonist antibody, a blocking antibody, a targeting antibody, a fragment thereof, or a combination thereof.

The terms "individual," "subject," "host," and "patient," are used interchangeably herein and refer to any mammalian subject for whom diagnosis, treatment, or therapy is desired, particularly humans. The compositions and methods described herein are applicable to both human therapy and veterinary applications. In some aspects, the subject is a mammal, and in other aspects the subject is a human. As used herein, a "mammalian subject" includes all mammals, including without limitation, humans, domestic animals (e.g., dogs, cats and the like), farm animals (e.g., cows, sheep, pigs, horses and the like) and laboratory animals (e.g., monkey, rats, mice, rabbits, guinea pigs and the like).

As used herein, the term "substantially free" means that the sample comprising EVs, e.g., exosomes, comprise less than 10% of macromolecules by mass/volume (m/v) percentage concentration. Some fractions may contain less than 0.001%, less than 0.01%, less than 0.05%, less than 0.1%, less than 0.2%, less than 0.3%, less than 0.4%, less than 0.5%, less than 0.6%, less than 0.7%, less than 0.8%, less than 0.9%, less than 1%, less than 2%, less than 3%, less than 4%, less than 5%, less than 6%, less than 7%, less than 8%, less than 9%, or less than 10% (m/v) of macromolecules.

As used herein, the term "macromolecule" means nucleic acids, contaminant proteins, lipids, carbohydrates, metabolites, or a combination thereof.

As used herein, the term "conventional exosome protein" means a protein previously known to be enriched in exosomes, including but is not limited to CD9, CD63, CD81, PDGFR, GPI anchor proteins, lactadherin LAMP2, and LAMP2B, a fragment thereof, or a peptide that binds thereto.

II. Methods of the Disclosure

Described herein are high-throughput methods for identifying one or more binding, wash and/or elution parameters (i.e., chromatography operational parameters) for a chromatography, such as those that can be used to purify EVs (e.g., exosomes) from a sample comprising the EVs and an impurity. In some aspects, the method of identifying one or more chromatography operational parameters (e.g., binding parameters) comprises (i) contacting the sample to a chromatography resin or medium under a plurality of chromatography operational parameters (e.g., binding parameters), (ii) collecting a fraction comprising the EV or impurity from (i), and (iii) determining an EV yield, impurity recovery, and/or EV ligand density from (ii). Also described herein are high-throughput methods for screening one or more chromatography reagents (e.g., resins) for purifying EVs (e.g., exosomes) from a sample comprising the EVs and an impurity. In some aspects, a method of screening one or more chromatography reagents comprises (i) contacting the sample to the one or more chromatography reagents (e.g., resins) under a plurality of chromatography operational parameters (e.g., binding parameters); (ii) collecting a fraction comprising the EV or impurity from (i), and (iii) determining the EV yield, impurity recovery, and/or EV ligand density from (ii). As described herein, the one or more chromatography operational parameters (e.g., binding parameters) and/or one or more chromatography reagents identified with the present disclosure can improve one or more aspects of an EV (e.g., exosome) purification process. Accordingly, in some aspects, the present disclosure is directed to a method of purifying an EV from a sample to improve an EV yield, improve EV ligand density, and/or reduce impurity recovery comprising: (i) contacting the sample to a chromatography resin or medium under a plurality of chromatography operational parameters (e.g., binding parameters), (ii) collecting a fraction comprising the EV or impurity from (i), and (iii) determining an EV yield, impurity recovery, and/or EV ligand density from (ii).

In some aspects, the contacting of the sample to the chromatography resin or medium can occur in any suitable apparatus. In some aspects, the contacting can occur as a single stage chromatography process. For example, in certain aspects, the contacting can occur in a multi-well microplate with loose beads (resins) suspended in each of the wells. In such aspects, the sample comprising the molecule of interest can be added to the wells of the microplate, which can be agitated to promote the interaction between a ligand (e.g., EVs, e.g., exosomes) in a sample with the beads. In certain aspects, the contacting can occur with immobilized resins, e.g., packed in a miniature columns, which then can be evaluated, e.g., using convective down-flow through with a displacement pipette or liquid handling robot.

In some aspects, the above high-throughput methods disclosed herein can further comprise iv) adjusting at least one of the plurality of chromatography operational parameters (e.g., binding parameters) and repeating steps (i) to (iii). In certain aspects, adjusting at least one of the chromatography operational parameters (e.g., binding parameters) can comprise increasing and/or decreasing the concentration of a chromatography operational parameter (e.g., binding parameter (e.g., sodium concentration)). In some aspects, adjusting at least one of the chromatography operational parameters (e.g., binding parameters) can comprise replacing a chromatography operational parameter (e.g., binding parameter) with a different corresponding chromatography operational parameter (e.g., binding parameter (e.g., using potassium salt instead of sodium salt)). In certain aspects, adjusting at least one of the chromatography operational parameters (e.g., binding parameters) can comprise increasing and/or decreasing the pH. In certain aspects, adjusting at least one of the chromatography operational parameters (e.g., binding parameters) can comprise increasing and/or decreasing the sodium concentration. In further aspects, adjusting at least one of the chromatography operational parameters (e.g., binding parameters) can comprise both increasing and/or decreasing the pH and increasing and/or decreasing the sodium concentration. In some aspects, the high-throughput methods disclosed herein further comprise repeating steps (i) to (iv) until the desired level of EV yield, EV ligand density, and/or impurity recovery is obtained (e.g., such as those described herein as being optimal for EV purification).

As used herein, the term "plurality of chromatography operational parameters" refers to two or more, e.g., about 2, about 5, about 10, about 15, about 30, about 40, about 50, about 70, about 80, about 90, about 96, about 100, about 150, about 200, about 250, about 300, about 350, about 384, about 400, about 500, about 600, about 700, about 900, about 1000, about 1536, about 2000, about 3000, or more chromatography operational parameters (e.g., those disclosed herein). In some aspects, the plurality of chromatography operational parameters refers to about 50 to about 100, e.g., about 96 chromatography operational parameters. In some aspects, the plurality of chromatography operational parameters refers to about 300 to about 400, e.g., about 384 chromatography operational parameters. In some aspects, the plurality of chromatography operational parameters refers to about 1000 to about 1600, e.g., about 1536 chromatography operational parameters.

As used herein, the term "plurality of binding parameters" refers to two or more, e.g., about 2, about 5, about 10, about 15, about 30, about 40, about 50, about 70, about 80, about 90, about 96, about 100, about 150, about 200, about 250, about 300, about 350, about 384, about 400, about 500, about 600, about 700, about 900, about 1000, about 1536, about 2000, about 3000, or more binding parameters (e.g., those disclosed herein). In some aspects, the plurality of binding parameters refers to about 50 to about 100, e.g., about 96 binding parameters. In some aspects, the plurality of binding parameters refers to about 300 to about 400, e.g., about 384 binding parameters. In some aspects, the plurality of binding parameters refers to about 1000 to about 1600, e.g., about 1536 binding parameters.

As described herein, depending on the cells from which they are produced ("producer cells"), EVs (e.g., exosomes) can comprise different lipids, proteins, carbohydrates, and/or nucleic acids. In some aspects, the producer cell can be a mammalian cell line, a plant cell line, an insect cell line, a fungi cell line, or a prokaryotic cell line. In certain aspects, the producer cell is a mammalian cell line. Non-limiting examples of mammalian cell lines include: a human embryonic kidney (HEK) cell line, a Chinese hamster ovary (CHO) cell line, an HT-1080 cell line, a HeLa cell line, a PERC-6 cell line, a CEVEC cell line, a fibroblast cell line, an amniocyte cell line, an epithelial cell line, a mesenchymal stem cell (MSC) cell line, and combinations thereof. In certain aspects, the mammalian cell line comprises HEK-293 cells, BJ human foreskin fibroblast cells, fHDF fibroblast cells, AGE.HN® neuronal precursor cells, CAP® amniocyte cells, adipose mesenchymal stem cells, RPTEC/TERT1 cells, or combinations thereof. In some aspects, the producer cell is a primary cell. In certain aspects, the primary cell can be a primary mammalian cell, a primary plant cell, a primary insect cell, a primary fungi cell, or a primary prokaryotic cell. In some aspects, the producer cell is not an immune cell, such an antigen presenting cell, a T cell, a B cell, a natural killer cell (NK cell), a macrophage, a T helper cell, or a regulatory T cell (Treg cell). In other aspects, the producer cell is not an antigen presenting cell (e.g., dendritic cells, macrophages, B cells, mast cells, neutrophils, Kupffer-Browicz cell, or a cell derived from any such cells).

EVs (e.g., exosomes) can also be modified to express certain molecules (e.g., exogenous biologically active molecules disclosed herein), such that EVs produced from the same producer cell can also comprise different lipids, proteins, carbohydrates, and/or nucleic acids. Such differences can affect the conditions (e.g., chromatography operational parameters, e.g., binding parameters) and/or reagents required for the purification of different EVs (e.g., exosomes) from a sample. Accordingly, in certain aspects, a distinct advantage of the present methods over those available in the art is the ability to screen numerous variables (e.g., chromatography operational parameters, e.g., binding parameters) in a relatively short period of time, and thereby, quickly identify conditions and/or reagents that are conducive for the purification of particular EVs (e.g., exosomes) using chromatography. In some aspects, the plurality of chromatography operational parameters (e.g., binding parameters (e.g., those disclosed herein)) can be assessed in a single assay.

IIA. Chromatography Operational Parameters (e.g., Binding, Wash, and/or Elution Parameters)

In some aspects, the methods disclosed herein can be used to identify any property of exosomes or impurities. In certain aspects, these properties can be quantified with analytical chromatography run with a high pressure liquid chromatography (HPLC) or ultra high pressure liquid chromatography (UPLC) apparatus. In some aspects, the chromatography is size exclusion chromatography (e.g., size exclusion high-performance liquid chromatography (SEC-HPLC)). In further aspects, the chromatography is ion-exchange chromatography. In certain aspects, the ion-exchange chromatography is a strong cation exchange chromatography. In further aspects, the chromatography is an anion exchange high-performance liquid chromatography (AEX-HPLC). In certain aspects, the chromatography is an ion-pairing reversed-phase chromatography (IPRP-HPLC). Non-limiting examples of other chromatography that are relevant for the present disclosure include affinity chromatography, mixed-mode chromatography, hydrophobic interaction chromatography, hydroxyapatite chromatography, immobilized metal affinity chromatography, or any combination thereof.

In certain aspects, the chromatography operational parameters (e.g., binding parameters) comprise a plurality of pHs, a plurality of weak acids and/or conjugate bases, a plurality of alcohols, a plurality of carbohydrates, a plurality of detergents, a plurality of chaotropic agents, a plurality of kosmotropic agents, a plurality of mass challenges, a plurality of residence times, a plurality of characteristic charges, a plurality of uptake times, a plurality of desorption times, a plurality of temperatures, a plurality of kinetic parameters, a plurality of diffusion rates, a plurality of mass transport rates, a plurality of binding coefficient, a plurality of thermodynamic binding equilibria, a plurality of salt concentrations, a plurality of buffers, or any combination thereof. As used herein, the term "plurality" refers to two or more, three or more, four or more, five or more, six or more, seven or more, eight or more, nine or more, or ten or more.

In some aspects, the chromatography operational parameters (e.g., binding parameters) comprise a plurality of pHs. In certain aspects, the plurality of pHs is between 0 and 14. In further aspects, the plurality of pHs is about 1, about 2, about 3, about 4, about 5, about 6, about 7, about 8, about 9, about 10, about 11, about 12, or about 13.

In some aspects, the chromatography operational parameters (e.g., binding parameters) comprise a plurality of salts. In certain aspects, the plurality of salts can comprise different types of salts. Non-limiting examples of salts that can be used with the present disclosure include a sodium salt, ammonium salt, calcium salt, potassium salt, or any combination thereof. In some aspects, the plurality of salts can comprise a single type of salt (e.g., sodium salt) but at a plurality of salt concentrations. In certain aspects, the plurality of salt concentrations is between about 0 M to about 10 M. In some aspects, the plurality of salt concentrations is between about 0 M to about 4 M. In certain aspects, the salt concentration is about 0 M, about 0.5 M, about 1 M, about 1.5 M, about 2 M, about 2.5 M, about 3 M. about 3.5 M or about 4 M. In further aspects, the plurality of salts can comprise both different types of salts and different salt concentrations. In certain aspects, the plurality of salts comprises a sodium salt at a concentration between about 0 M and about 4 M.

In some aspects, the chromatography operational parameters (e.g., binding parameters) comprise a plurality of weak acids and/or conjugate bases. In certain aspects, the plurality of weak acids and/or conjugate bases comprise different types of weak acids and/or conjugate bases. In some aspects, the different types of weak acids and/or conjugate bases comprise Tris, acetate, phosphate, MES, MOPS, HEPES, Bis-Tris, citrate, carbonate, histidine, or any combination thereof. In some aspects, the plurality of weak acids and/or conjugate bases can differ in concentration. For instance, in certain aspects, the plurality of weak acids and/or conjugate bases can comprise a single type of weak acid and/or conjugate base but at a plurality of concentrations. In some aspects, the plurality of concentrations is between about 0 M to about 5 M. In certain aspects, the plurality of concentrations is between about 0 M to about 1 M. In some aspects, the concentration of weak acids and/or conjugate bases is about 0 M, about 0.1 M, about 0.2 M, about 0.3 M, about 0.4 M, about 0.5 M, about 0.6 M, about 0.7 M, about 0.8 M, about 0.9 M, or about 1.0 M. In some aspects, the plurality of weak acids and/or conjugate bases comprises different types of weak acids and/or conjugate bases, wherein one or more of the weak acids and/or conjugate bases are at different concentrations.

In some aspects, the chromatography operational parameters (e.g., binding parameters) comprise a plurality of alcohols. In certain aspects, the plurality of alcohols can differ in type. Non-limiting examples of different types of alcohols that can be used with the present disclosure include methanol, ethanol, polyhydric alcohols, polyvinyl alcohol, or any combination thereof. In some aspects, the plurality of alcohols can comprise a single type of alcohol but at a plurality of alcohol concentrations. In some aspects, the plurality of alcohols comprises both different types of alcohols and different alcohol concentrations.

In some aspects, the chromatography operational parameters (e.g., binding parameters) comprise a plurality of carbohydrates. In certain aspects, the plurality of carbohydrates can comprise different types of carbohydrates. Non-limiting examples of carbohydrates that can be used with the present disclosure include monosaccharides (e.g., fructose, maltose, galactose, glucose, D-mannose, sorbose), disaccharides (e.g., lactose, sucrose, trehalose, cellobiose), polysaccharides (e.g., raffinose, melezitose, maltodextrins, dextrans, starches), alditols (e.g., mannitol, xylitol, malititol, lactitol, xylitol sorbitol), or any combination thereof. In some aspects, the plurality of carbohydrates can comprise a single type of carbohydrate but at a plurality of concentrations. In some aspects, the plurality of carbohydrates can differ in both type and concentration.

In some aspects, the chromatography operational parameters (e.g., binding parameters) comprise a plurality of detergents. In certain aspects, the plurality of detergents comprises different types of detergents. In some aspects, the different types of detergents comprise an ionic detergent (e.g., sodium dodecyl sulfate (SDS), sodium deoxycholate, sodium cholate, sarkosyl), non-ionic detergent (e.g., Triton X-100, DDM, digitonin, Tween 20, Tween 80), zwitterionic detergent (e.g., CHAPS), or any combination thereof. In certain aspects, the plurality of detergents comprises a single type of detergent but a plurality of concentrations. In some aspects, the plurality of detergents comprises both different types of detergents and different detergent concentrations.

In some aspects, the chromatography operational parameters (e.g., binding parameters) comprise a plurality of chaotropic agents. As used herein, the term "chaotropic agent" or "chaotropes" refers to any agent that can disrupt the hydrogen bonding network between water molecules. In some aspects, chaotropes can increase the solubility of nonpolar solvent particles and help destabilize solute aggregates. In certain aspects, the plurality of chaotropic agents comprises different types of chaotropic agents. Non-limiting examples of chaotropic agents that can be used with the present disclosure include urea, guanidinium chloride, thiocyanate salt (e.g., sodium thiocyanate, potassium thiocyanate, or ammonium thiocyanate), n-butanol, ethanol, lithium perchlorate, lithium acetate, magnesium chloride, phenol, 2-propanol, sodium dodecyl sulfate, thiourea, or any combination thereof. In certain aspects, the plurality of chaotropic agents comprises a single type of chaotropic agent but at a plurality of concentrations. In some aspects, the plurality of chaotropic agents comprises both different types of chaotropic agents and different chaotropic agent concentrations.

In some aspects, the chromatography operational parameters (e.g., binding parameters) comprise a plurality of kosmotropic agents. As used herein, the term "kosmotropic agent" or "kosmotropes" refers to any agent that can promote the stability and structure of water molecules, which in turn help stabilizes intramolecular interactions in macromolecules such as proteins. In certain aspects, the plurality of kosmotropic agents comprises different types of kosmotropic agents. In certain aspects, the plurality of kosmotropic agents comprises a single type of kosmotropic agent but at a plurality of concentrations. In some aspects, the plurality of kosmotropic agents comprises both different types of kosmotropic agents and different kosmotropic agent concentrations. Non-limiting examples of kosmotropic agents include carbonate ($[CO_3]^{2-}$), sulfate ($[SO_4]^{2-}$), hydrogen phosphate ($[HPO_4]^{2-}$), magnesium ($Mg^{2+}$), lithium ($Li^+$), zinc ($Zn^{2+}$), aluminum ($Al^{3+}$), or combinations thereof.

In some aspects, the chromatography operational parameters (e.g., binding parameters) comprise a plurality of mass challenge. As used herein, the term "mass challenge" refers to the amount of sample (e.g., comprising an EV and/or impurity) that is loaded onto a chromatography column.

In some aspects, the chromatography operational parameters (e.g., binding parameters) comprise a plurality of residence time. As used herein, the term "residence time" refers to the amount of time that a sample (e.g., comprising an EV and/or impurity) is in contact with the chromatography resin.

In some aspects, the chromatography operational parameters (e.g., binding parameters) comprise a plurality of temperatures.

In some aspects, the chromatography operational parameters (e.g., binding parameters) comprise at least two, three, four, five, six, seven, eight, nine, ten, or all of the chromatography operational parameters (e.g., binding parameters) disclosed herein. In further aspects, the chromatography operational parameters (e.g., binding parameters) can further comprise other chromatography operational parameters (e.g., binding parameters) that are known in the art for purifying molecules from a sample using chromatography. In certain aspects, the chromatography operational parameters (e.g., binding parameters) comprise a plurality of salt concentrations and a plurality of pHs.

II.B. Collection of Fraction Comprising an EV (e.g., Exosome)

As described herein, after a sample (e.g., comprising an EV and an impurity) is loaded onto a chromatography column (i.e., contacting to a chromatography resin or medium), the methods disclosed herein comprise collecting a fraction comprising the EV. In some aspects, the fraction can be collected by any method known in the art.

In some aspects, the fraction comprising the EV is collected through a flow-through mode. As used herein, the term "flow-through mode" refers to a separation technique in which at least one molecule of interest (e.g., EVs, e.g., exosomes) contained in a sample is intended to flow through a chromatographic resin or medium, while at least one molecule of non-interest (e.g., an impurity) binds to the chromatographic resin or medium. In certain aspects, the partition coefficient for the molecule of interest (e.g., EVs, e.g., exosomes) in the flow-through mode is less than about 0.1. As used herein, the term "partition coefficient" (Kp) refers to the ratio of the concentration of the molecule (e.g., EV, e.g., exosome) bound to the chromatographic resin or medium (Q) to the concentration of the molecule (e.g., EV, e.g., exosome) in the sample at equilibrium. In some aspects, the partition coefficient refers to the strength of the interaction between the bound molecule and the chromatography column.

In some aspects, the fraction comprising the EV is collected through a bind-and-elute mode. As used herein, the term "bind-and-elute mode" refers to a separation technique in which at least one molecule (e.g., EVs, e.g., exosomes) contained in a sample binds to a chromatographic resin or medium. In certain aspects, the partition coefficient for the molecule of interest (e.g., EV, e.g., exosome) in the bind-and-elute mode is greater than about 20. In some aspects, the bound molecule (e.g., EVs, e.g., exosomes) in this mode is eluted during the elution phase. In certain aspects, the bind-and-elute mode can further comprise one or more additional steps that help increase the recovery of the molecule of interest (e.g., EVs, e.g., exosomes). In some aspects, the bind-and-elute mode can additionally comprise one or more post-load washes (i.e., washes that are added to the column resin after the initial loading and flowthrough has occurred) that selectively desorb any impurities bound to the chromatographic resin or medium. In certain aspects, the high-throughput screening methods described herein can be used to identify the parameters for such post-load washes. In some aspects, the bind-and-elute mode can further comprise the use of an elution that selectively desorb the molecule of interest (e.g., EVs, e.g., exosomes) without desorbing any impurities bound to the chromatographic resin or medium. In certain aspects, the high-throughput screening methods described herein can be used to identify the parameters for such post-load washes. In some aspects, the bind-and-elute mode can also comprise the use of aggressive elution or strip agents that selectively removes any tightly bound impurities and prepare the chromatographic resin or medium for additional use.

In some aspects, the fraction comprising the EV is collected through a weak partitioning mode. As used herein, the term "weak partitioning mode" refers to a separation technique in which at least one molecule of interest (e.g., EVs, e.g., exosomes) and at least one impurity contained in a sample both bind to a chromatographic resin or medium. In certain aspects, the partition coefficient for the molecule of interest (e.g., EVs, e.g., exosomes) and/or the impurity is at least about 0.1. In some aspects, the partition coefficient for the molecule of interest (e.g., EVs, e.g., exosomes) and the partition coefficient for the impurity are different. In certain aspects, the recovery of the molecule of interest (e.g., EVs, e.g., exosomes) can be enhanced with the inclusion of one or more post-load washes (i.e., washes that are added to the column resin after the initial loading and flowthrough has occurred).

II.C. Determination of EV (e.g., Exosome) Yield, Impurity Recovery, and/or EV Ligand Density As described herein, the methods of the present disclosure comprise determining the EV (e.g., exosome) yield, impurity recovery, and/or EV (e.g., exosome) ligand density from a fraction collected in a chromatography. As used herein, the term "EV yield" refers to the number (i.e., quantity) of EV (e.g., exosome) particles present in the collected fraction compared to the number of EV (e.g., exosome) particles present in the original sample (i.e., prior to the separation using chromatography). As used herein, the term "EV ligand density" refers to the number of a specific-ligand expressed on a single EV (e.g., exosome) particle. As described herein, EVs (e.g., exosomes) can express various ligands or molecules depending on the producer cells from which they originate or any modifications made the EVs. Accordingly, an EV (e.g., exosome) can express a wide variety of different ligands. In some aspects, a ligand is an exogenous biologically active molecule (e.g., payload or targeting moiety). In certain aspects, a ligand is a scaffold moiety (e.g., Scaffold X or Scaffold Y). As used herein, the term "impurity recovery" refers to the amount of impurity present in the collected fraction compared to the amount of impurity present in the original sample (i.e., prior to the separation using chromatography).

In some aspects, the EV yield is greater than about 5%, greater than about 10%, greater than about 20%, greater than about 30%, greater than about 40%, greater than about 50%, greater than about 60%, greater than about 70%, greater than about 80%, greater than about 90% or more. In some aspects, the EV ligand density is at least about 5 ligands/EV, at least about 10 ligands/EV, at least about $10^2$ ligands/EV, at least about $10^3$ ligands/EV, at least about $10^3$ ligands/EV, at least about $10^4$ ligands/EV, or at least about $10^6$ ligands/EV. In some aspects, the impurity recovery is less than about 50%, less than about 40%, less than about 30%, less than about 20%, less than about 10%, less than about 9%, less than about 8%, less than about 7%, less than about 6%, less than about 5%, less than about 4%, less than about 3%, less than about 2%, or less than about 1%.

In some aspects, one or more chromatography operational parameters (e.g., binding parameters) are optimal for purifying an EV (e.g., exosome), wherein the EV yield is increased compared to a reference (e.g., EV yield of a sample using different chromatography operational parameters (e.g., binding parameters)). In some aspects, one or more chromatography operational parameters (e.g., binding parameters) are optimal for purifying an EV (e.g., exosome), wherein the EV ligand density is increased compared to a reference (e.g., EV ligand density of the sample prior to contacting to a chromatography resin or medium). In some aspects, one or more chromatography operational parameters (e.g., binding parameters) are optimal for purifying an EV (e.g., exosome), wherein the impurity recovery is decreased compared to a reference (e.g., impurity recovery of a sample using different chromatography operational parameters (e.g., binding parameters)).

As described herein, the present disclosure also relates to high-throughput methods for screening one or more chromatography reagents for purifying EVs (e.g., exosomes) from a sample. In certain aspects, the methods disclosed herein can be used to screen any chromatography reagents known in the art. In some aspects, a chromatography reagent that can screened with the high-throughput methods disclosed herein include resins and excipient wash solutions.

In some aspects, the one or more chromatography reagents are optimal for purifying an EV (e.g., exosome), wherein the EV yield is increased compared to a reference (e.g., EV yield of a sample using different chromatography reagents). In some aspects, the one or more chromatography reagents are optimal for purifying an EV (e.g., exosome), wherein the impurity recovery is decreased compared to a reference (e.g., impurity recovery of a sample using different chromatography reagents). In further aspects, the one or more chromatography reagents are optimal for purifying an EV (e.g., exosome), wherein the EV ligand density is increased compared to a reference (e.g., EV ligand density of the sample prior to contacting to the chromatography reagents identified with the present methods).

The EV yield, EV ligand density, and/or impurity recovery for purposes of the present disclosure can be determined using any methods known in the art for quantitating the amount of EVs (e.g., exosomes), impurities present in a solution, and/or ligands expressed on an EV (e.g., exosome). Non-limiting examples of such methods are described further below. Other methods (e.g., for quantifying EV yield) include antibody-tracked exosome dispersion (e.g., flow-induced dispersion analysis (FDA)). See Pedersen et al., *Methods Mol Biol* 1972: 109-123 (2019), which is incorporated herein by reference in its entirety. In some aspects, EV yield can also be measured by quantifying the amount of cholesterol present in a sample.

While some of the methods provided below are described in the context of determining the EV (e.g., exosome) yield, it will be apparent to those in the art that the disclosed methods could also be used for other relevant purposes, e.g., determining the impurity recovery of a solution (e.g., the collected fraction or the sample prior to the chromatography separation) and/or determining the EV (e.g., exosome) ligand density. Accordingly, in some aspects, the EV (e.g., exosome) yield, EV (e.g., exosome) ligand density, and/or the impurity recovery are determined using the same method (e.g., measuring a light scattering emission signal, intrinsic fluorescence signaling, and/or absorbance). In other aspects, the EV yield, EV ligand density, and/or the impurity recovery are determined using different methods. For instance, in certain aspects, the EV yield is determined using one of the methods described below (e.g., measuring a light scattering emission signal, intrinsic fluorescence signaling, and/or absorbance) and the impurity recovery is determined using a different assay. Non-limiting examples of assays that can be used to determine the impurity recovery and/or the EV ligand density include ELISA or Alphalisa.

Detection of Light Scattering Emission Signal

In some aspects, the EV (e.g., exosome) yield is determined by measuring a light scattering emission signal of a solution, wherein the light scattering emission signal is indicative of the presence of one or more EVs (e.g., exosomes) in a solution. In certain aspects, the EV (e.g., exosome) yield is determined by comparing the light scattering emission signal of the collected fraction to the light scattering emission signal of the sample prior to contacting the sample to a chromatography resin or medium. As described herein, in some aspects, the light scattering can be measured using absorbance (e.g., UV). In certain aspects, the absorbance (e.g., UV) is measured at a wavelength between about 320 nm to about 1100 nm. In some aspects, the absorbance (e.g., UV) is measured at a wavelength of about 320 nm, 400 nm, 405 nm, or about 600 nm.

In some aspects, the light scattering emission signal of a solution (e.g., the collected fraction or the sample prior to the chromatography separation) is detected in a single step. In other aspects, the light scattering emission signal is detected in multiple steps. In some aspects, the light scattering emission signal of a solution (e.g., the collected fraction or the sample prior to the chromatography separation) is detected after the solution has been further processed or stored for a period of time. In certain aspects, the light scattering emission of a solution (e.g., the collected fraction or the sample prior to the chromatography separation) is detected immediately after collection. For example, in some aspects, the fraction collected after contacting the sample to a chromatography resin or medium is assessed for its light scattering emission signal immediately after the collection. In other aspects, the fraction collected after contacting the sample to a chromatography resin or medium is assessed for its light scattering emission signal after further processing.

In some aspects, the relative amounts or concentrations of EVs (e.g., exosomes) in a solution are determined or assessed by measurement of light scattering using standard techniques. In some aspects, the relative amounts or concentrations of EVs (e.g., exosomes) in a solution are determined by measuring a light scattering signal emitted from the EVs (e.g., exosomes) ("emission signal") in the solution after the solution is excited with a light source. Detection and/or measurement of light scattering emission signal can be performed manually by multi-angle light scattering, dynamic light scattering, nanoparticle tracking assay, X-ray scattering, neutron scattering wide-angle X-ray scattering, small-angle X-ray scattering, ALPHALISA®, two-dimensional liquid chromatography, or any other method known in the art. Examples of the detectors for the light scattering emission signals include, but not limited to, optical density detectors, dynamic and static light scattering detectors, evaporative light scattering detectors, photodiode array detector, fluorescence detector, UV detector, tunable UV detector, multi-channel fluorescence detector, dual wavelength absorbance detector, multichannel optical density detector, and scanning fluorescence detector. In certain aspects, light scattering emission signal of a solution (e.g., the collected fraction or the sample prior to the chromatography separation) is determined or measured using a microplate reader or any other acceptable method known in the art for the detection and measurement of light scattering in a solution. In some aspects, the light scattering emission signal is not a fluorescence signal.

In some aspects, the light scattering profile of EVs (e.g., exosomes) present in a solution is detected on a optical density detector and/or a fluorescence detector. In certain aspects, the light scattering profile is generated by exposing the solution (e.g., the collected fraction or the sample prior to the chromatography separation) to an excitation wavelength of between about 280 nm to about 700 nm. In some aspects, the light scattering profile is detected by measuring an emission wavelength that is about 0 nm to about 20 nm longer or shorter than the excitation wavelength. In certain aspects, the emission wavelength is between about 260 nm to about 720 nm.

In some aspects, the light source used to excite a solution comprising an EV (e.g., exosome) (e.g., the collected fraction or the sample prior to the chromatography separation) has an excitation wavelength ranging from about 200 nm to about 900 nm. In certain aspects, the light source has an excitation wavelength ranging from about 200 nm to about 800 nm, from about 200 nm to about 700 nm, from about 210 nm to about 900 nm, from about 210 nm to about 800 nm, from about 210 nm to about 700 nm, from about 220 nm to about 900 nm, from about 220 nm to about 800 nm, from about 220 nm to about 700 nm, from about 230 nm to about 900 nm, from about 230 nm to about 800 nm, from about 230 nm to about 700 nm, from about 240 nm to about 900 nm, from about 240 nm to about 800 nm, from about 240 nm to about 700 nm, from about 250 nm to about 900 nm, from about 200 nm to about 800 nm, from about 250 nm to about 700 nm, from about 260 nm to about 900 nm, from about 260 nm to about 800 nm, from about 260 nm to about 700 nm, from about 270 nm to about 900 nm, from about 270 nm to about 800 nm, from about 270 nm to about 700 nm, from about 280 nm to about 900 nm, or from about 280 nm to about 800 nm.

In some aspects, the light source has an excitation wavelength ranging from about 280 nm to about 700 nm. In some aspects, the light source has an excitation wavelength ranging from about 300 nm to about 700 nm, from about 320 nm to about 700 nm, from about 340 nm to about 700 nm, from about 360 nm to about 700 nm, from about 380 nm to about 700 nm, from about 400 nm to about 700 nm, from about 420 nm to about 700 nm, from about 440 nm to about 700 nm, from about 460 nm to about 700 nm, from about 300 nm to about 660 nm, from about 320 nm to about 660 nm, from about 340 nm to about 660 nm, from about 360 nm to about 660 nm, from about 380 nm to about 660 nm, from about 400 nm to about 660 nm, from about 420 nm to about 660 nm, from about 440 nm to about 660 nm, from about 460 nm to about 660 nm, from about 300 nm to about 640 nm, from about 320 nm to about 640 nm, from about 340 nm to about 640 nm, from about 360 nm to about 640 nm, from about 380 nm to about 640 nm, from about 400 nm to about 640 nm, from about 420 nm to about 640 nm, from about 440 nm to about 640 nm, from about 460 nm to about 640 nm, from about 400 nm to about 600 nm, from about 400 nm to about 500 nm, from about 450 nm to about 500 nm, from about 420 nm to about 520 nm, or from about 440 nm to about 540 nm.

In some aspects, the light source has an excitation wavelength ranging from about 400 nm to about 500 nm. In some aspects, the light source has an excitation wavelength ranging from about 400 nm to about 410 nm. In some aspects, the light source has an excitation wavelength ranging from about 410 nm to about 420 nm. In some aspects, the light source has an excitation wavelength ranging from about 420 nm to about 430 nm. In some aspects, the light source has an excitation wavelength ranging from about 430 nm to about 440 nm. In some aspects, the light source has an excitation wavelength ranging from about 440 nm to about 450 nm. In some aspects, the light source has an excitation wavelength ranging from about 450 nm to about 460 nm. In some aspects, the light source has an excitation wavelength ranging from about 460 nm to about 470 nm. In some aspects, the light source has an excitation wavelength ranging from about 470 nm to about 480 nm. In some aspects, the light source has an excitation wavelength ranging from about 480 nm to about 490 nm. In some aspects, the light source has an excitation wavelength ranging from about 490 nm to about 500 nm.

In some aspects, the light source has an excitation wavelength of about 400 nm. In some aspects, the light source has an excitation wavelength of about 400 nm, about 410 nm, about 420 nm, about 430 nm, about 440 nm, about 450 nm, about 460 nm, about 470 nm, about 480 nm, about 490 nm, or about 500 nm. In some aspects, the light source has an excitation wavelength of about 400 nm. In some aspects, the light source has an excitation wavelength of about 410 nm. In some aspects, the light source has an excitation wavelength of about 420 nm. In some aspects, the light source has an excitation wavelength of about 430 nm. In some aspects, the light source has an excitation wavelength of about 440 nm. In some aspects, the light source has an excitation wavelength of about 450 nm. In some aspects, the light source has an excitation wavelength of about 460 nm. In some aspects, the light source has an excitation wavelength of about 470 nm. In some aspects, the light source has an excitation wavelength of about 480 nm. In some aspects, the light source has an excitation wavelength of about 490 nm. In some aspects, the light source has an excitation wavelength of about 500 nm.

In some aspects, the light scattering emission signal has an emission wavelength equal to or longer than the excitation wavelength. In some aspects, the emission wavelength is less than about 20 nm, less than about 19 nm, less than about 18 nm, less than about 17 nm, less than about 16 nm, less than about 15 nm, less than about 14 nm, less than about 13 nm, less than about 12 nm, less than about 11 nm, less than about 10 nm, less than about 9 nm, less than about 8 nm, less than about 7 nm, less than about 6 nm, less than about 5 nm, less than about 4 nm, less than about 3 nm, less than about 2 nm, less than about 1 nm, or less than about 0.5 nm longer than the excitation wavelength.

In some aspects, the difference between the emission and excitation wavelengths ranges from about 0 nm to about 1 nm, about 0 nm to about 2 nm, about 0 nm to about 3 nm, about 0 nm to about 4 nm, about 0 nm to about 5 nm, about 0 nm to about 6 nm, about 0 nm to about 7 nm, about 0 nm to about 8 nm, about 0 nm to about 9 nm, or about 0 nm to about 10 nm. In some aspects, the difference between the emission and excitation wavelengths ranges from about 1 nm to about 2 nm, about 1 nm to about 3 nm, about 1 nm to about 4 nm, about 1 nm to about 5 nm, about 1 nm to about 6 nm, about 1 nm to about 7 nm, about 1 nm to about 8 nm, about 1 nm to about 9 nm, or about 1 nm to about 10 nm. In some aspects, the difference between the emission and excitation wavelengths ranges from about 2 nm to about 3 nm, about 2 nm to about 4 nm, about 2 nm to about 5 nm, about 2 nm to about 6 nm, about 2 nm to about 7 nm, about 2 nm to about 8 nm, about 2 nm to about 9 nm, about 2 nm to about 10 nm, about 3 nm to about 4 nm, about 3 nm to about 5 nm, about 3 nm to about 6 nm, about 3 nm to about 7 nm, about 3 nm to about 8 nm, about 3 nm to about 9 nm, about 3 nm to about 10 nm, about 4 nm to about 5 nm, about 4 nm to about 6 nm, about 4 nm to about 7 nm, about 4 nm to about 8 nm, about 4 nm to about 9 nm, about 4 nm to about 10 nm, about 5 nm to about 6 nm, about 5 nm to about 7 nm, about 5 nm to about 8 nm, about 5 nm to about 9 nm, about 5 nm to about 10 nm, about 6 nm to about 7 nm, about 6 nm to about 8 nm, about 6 nm to about 9 nm, about 6 nm to about 10 nm, about 7 nm to about 8 nm, about 7 nm to about 9 nm, about 7 nm to about 10 nm, about 8 nm to about 9 nm, about 8 nm to about 10 nm, or about 9 nm to about 10 nm.

In some aspects, the light scattering profile of EVs (e.g., exosomes) present in a solution is detected at 460 nm excitation and 470 nm emission. In certain aspects, the light scattering profile of EVs (e.g., exosomes) is detected at 460 nm excitation and 460 nm emission.

In some aspects, the light source has an excitation wavelength at about 450 nm to about 470 nm. In some aspects, the excitation wavelength is about 460 nm and the emission wavelength is about 460 nm to about 480 nm. In some aspects, the excitation wavelength is about 460 nm and the emission wavelength is about 460 nm, about 465 nm, about 470 nm, about 475 nm, or about 480 nm.

In some aspects, the excitation wavelength is about 450 nm and the emission wavelength is about 450 nm to about 470 nm. In some aspects, the excitation wavelength is about 450 nm and the emission wavelength is about 450 nm, about 455 nm, about 460 nm, about 465 nm, or about 470 nm. In some aspects, the excitation wavelength is about 470 nm and the emission wavelength is about 470 nm to about 490 nm.

In some aspects, the excitation wavelength is about 470 nm and the emission wavelength is about 470 nm, about 475 nm, about 480 nm, about 485 nm, or about 490 nm.

In some aspects, the excitation and emission wavelengths are selected so that the excitation wavelength is shorter than or equal to the emission wavelength. In some aspects, the excitation and emission wavelengths are selected so that the excitation wavelength is longer than or equal to the emission wavelength.

In some aspects, the excitation wavelength varies according to the membrane composition and/or payload composition of the EVs (e.g., exosomes) in a solution. In some aspects, the emission wavelength varies according to the membrane composition and/or payload composition of the EVs (e.g., exosomes) in a solution. In some aspects, the emission wavelength and/or excitation wavelength varies according to the homogeneity of the EV (e.g., exosome) preparation. In certain aspects, the excitation wavelength and/or emission wavelength used to detect the EVs (e.g., exosomes) varies according to the type of producer cell from which the EV (e.g., exosome) is derived. In some aspects, the excitation wavelength and/or emission wavelength used to detect the EVs (e.g., exosomes) varies according to the purity of the solution comprising the EVs.

In some aspects, the light scattering emission signal detected at a given wavelength, e.g., 460 nm to 480 nm when excited at 460 nm, indicates the purity of EVs (e.g., exosomes) in a solution. In some aspects, the light scattering emission signal detected at certain wavelengths, e.g., outside of 460 nm to 480 nm when excited at 460 nm, indicates the presence of contaminants in a solution. In some aspects, the light scattering emission signal indicates the concentration of the EVs (e.g., exosomes) in a solution. In some aspects, the light scattering emission signal indicates the concentration of contaminants in a solution.

Detection of Intrinsic Fluorescence Signal

In some aspects, the EV (e.g., exosome) yield is determined by measuring the intrinsic fluorescence signal of EVs in a solution (e.g., the collected fraction or the sample prior to the chromatography separation). In some aspects, the EV (e.g., exosome) yield is determined by comparing the intrinsic fluorescence signal of the collected fraction to the intrinsic fluorescence signal of the sample prior to the chromatographic separation (i.e., prior to contacting the sample to the chromatography resin or medium). In certain aspects, the intrinsic fluorescence signal is measured in addition to one or more other methods described herein for determining the EV (e.g., exosome) yield of a solution (e.g., measuring the light scattering emission signal).

In some aspects, the intrinsic fluorescence signal in a solution (e.g., the collected fraction or the sample prior to the chromatography separation) is detected in a single step. In other aspects, the intrinsic fluorescence signal is detected in multiple steps. In some aspects, the intrinsic fluorescence signal in a solution (e.g., the collected fraction or the sample prior to the chromatography separation) is detected after the solution has been further processed or stored for a period of time. In certain aspects, the intrinsic fluorescence signal is detected immediately after collecting the solution. For example, in some aspects, the fraction collected after contacting the sample to a chromatography resin or medium is assessed for its intrinsic fluorescence signal immediately after the collection. In other aspects, the fraction collected after contacting the sample to a chromatography resin or medium is assessed for its intrinsic fluorescence signal after further processing.

In some aspects, the intrinsic fluorescence is measured using a fluorescence spectroscopy. In some aspects, the intrinsic fluorescence signal is measured after a solution comprising the EVs (e.g., exosomes) (e.g., the collected fraction or the sample prior to the chromatography separation) is exposed to an excitation wavelength of about 280 nm. In certain aspects, the intrinsic fluorescence signal measured after the excitation can be due to proteins embedded in EVs (e.g., exosomes), proteins fused to the surface of EVs, or contaminants present in the solution comprising EVs (e.g., exosomes). In some aspects, the intrinsic fluorescence signal can be obtained as a result of the fluorescent emission of one or more amino acids within the EVs, e.g., aromatic amino acids.

In some aspects, the intrinsic fluorescence signal is emitted at a wavelength of about 350 nm. In certain aspects, the intrinsic fluorescence is emitted at a wavelength of about 300 nm, about 350 nm, about 400 nm, about 450 nm, about 500 nm, about 550 nm, about 600 nm, about 650 nm, or about 700 nm. In some aspects, the intrinsic fluorescence signal is measured by a fluorescence detector after the EVs (e.g., exosomes) in a solution are excited at an excitation wavelength of about 270 nm to about 280 nm. In certain aspects, the excitation wavelength is about 270 nm, about 274 nm, about 275 nm, about 278 nm, or about 280 nm.

Detection of Absorbance (e.g., UV)

In some aspects, the EV (e.g., exosome) yield is determined by measuring the absorbance (e.g., UV) of EVs in a solution (e.g., the collected fraction or the sample prior to the chromatography separation). In some aspects, the EV (e.g., exosome) yield is determined by comparing the absorbance (e.g., UV) for the collected fraction to the absorbance (e.g., UV) for the sample prior to the chromatographic separation (i.e., prior to contacting the sample to the chromatography resin or medium). In certain aspects, the absorbance (e.g., UV) is measured in addition to one or more other methods described herein for determining the EV (e.g., exosome) yield of a solution (e.g., measuring the light scattering emission signal or measuring the intrinsic fluorescence signal).

In some aspects, the absorbance (e.g., UV) of a solution (e.g., the collected fraction or the sample prior to the chromatography separation) is detected in a single step. In other aspects, the absorbance (e.g., UV) is detected in multiple steps. In some aspects, the absorbance (e.g., UV) of a solution (e.g., the collected fraction or the sample prior to the chromatography separation) is detected after the solution has been further processed or stored for a period of time. In certain aspects, the absorbance (e.g., UV) is measured immediately after collecting the solution. For example, in some aspects, the fraction collected after contacting the sample to a chromatography resin or medium is assessed for its absorbance (e.g., UV) immediately after the collection. In other aspects, the fraction collected after contacting the sample to a chromatography resin or medium is assessed for its absorbance after further processing.

In some aspects, the absorbance (e.g., UV) is measured by scanning the wavelength range from about 190 nm to about 380 nm. Proteins in solution absorb ultraviolet light with absorbance maxima at 200 and 280 nm. Amino acids with aromatic rings are the primary reason for the absorbance peak at 280 nm. Peptide bonds are primarily responsible for the peak at 200 nm. Secondary, tertiary, and quaternary structure all affect absorbance, therefore factors such as pH, ionic strength, etc. can alter the absorbance spectrum. In some aspects, the absorbance (e.g., UV) is measured after the solution is excited by a light at the wavelength of 280 nm. In some aspects, the absorbance (e.g., UV) is measured after the solution is excited by a light at the wavelength of 200 nm. In some aspects, absorbance (e.g., UV) is measured after the solution is excited by a light at the wavelength of 320 nm. In some aspects, the absorbance (e.g., UV) is measured after the solution is excited by a light at the wavelength of 405 nm. In some aspects, the absorbance (e.g., UV) is measured after the solution is excited by a light at the wavelength of 600 nm. In some aspects, the absorbance (e.g., UV) is measured by a optical density detector.

II.D. Calculation of Selectivity (α)

The methods disclosed herein can further comprise calculating selectivity (α) for an EV (e.g., exosome), e.g., using the EV yield and impurity recovery described above. In some aspects, by comparing the selectivity across an experiment, optimal chromatography operational parameters (e.g., binding parameters) for a given chromatographic separation of an EV (e.g., exosome) can be determined. In certain aspects, these optimal chromatography operational parameters (e.g., binding parameters) are conditions where EV (e.g., exosome) recovery is high, and impurity recovery is low. In certain aspects, selectivity (α) can be calculated with the following formula: partition coefficient (Kp) of tighter binding species (e.g., impurity)mpurity/partition coefficient of weaker binding species (e.g., EV).

II.E. Further Assessment and Characterization of EVs (e.g., Exosomes)

As described herein, EVs can vary in their structure and composition depending on the cells from which they are produced or due to external modifications. These differences can affect the chromatography operational parameters (e.g., binding parameters) and/or reagents required when purifying the EVs from a sample, e.g., with chromatography. Accordingly, the high-throughput methods disclosed herein can be used to identify chromatography operational parameters (e.g., binding parameters) and/or reagents for the purification of a diverse population of EVs (e.g., exosomes). The identity and concentrations of EVs (e.g., exosomes) purified from a sample using the chromatography operational parameters (e.g., binding parameters) and/or reagents identified with the present disclosure can be assessed and/or validated by any method known in the art.

For example, the identity and concentration of EVs (e.g., exosomes) is determined or assessed by counting the number of complexes in a population, e.g., by microscopy, by flow cytometry, or by hemacytometry. Alternatively, or in addition, the identity and/or concentration of the EVs (e.g., exosomes) is assessed by analysis of protein content of the complex, e.g., by flow cytometry, Western blot, immunoprecipitation, fluorescence spectroscopy, chemiluminescence, mass spectrometry, or absorbance spectroscopy. In certain aspects, the protein content assayed is a non-surface protein, e.g., an integral membrane protein, hemoglobin, adult hemoglobin, fetal hemoglobin, embryonic hemoglobin, or a cytoskeletal protein. In some aspects, the protein content assayed is a surface protein, e.g., a differentiation marker, a receptor, a co-receptor, a transporter, a glycoprotein. In certain aspects, the surface protein is selected from the list including, but not limited to, glycophorin A, CKIT, transferrin receptor, Band3, Kell, CD45, CD46, CD47, CD55, CD59, CR1, CD9, CD63 and CD81. In certain aspects, the identity of EVs (e.g., exosomes) is assessed by analysis of the receiver content of the EVs, e.g., by flow cytometry, Western blot, immunoprecipitation, fluorescence spectroscopy, chemiluminescence, mass spectrometry, or absorbance spectroscopy. For example, the identity of EVs can be assessed by the mRNA and/or miRNA content of the complexes, e.g., by RT-PCR, flow cytometry, or northern blot. The identity of the EVs can be assessed by nuclear material content, e.g., by flow cytometry, microscopy, or southern blot, using, e.g., a nuclear stain or a nucleic acid probe. Alternatively, or in addition, the identity of the EVs can be assessed by lipid content of the complexes, e.g., by flow cytometry, liquid chromatography, or by mass spectrometry.

In some aspects, the identity of the EVs (e.g., exosomes) is assessed and/or validated by metabolic activity of the complexes, e.g., by mass spectrometry, chemiluminescence, fluorescence spectroscopy, absorbance spectroscopy. In certain aspects, metabolic activity can be assessed by ATP consumption rate and/or by measuring 2,3-diphosphoglycerate (2,3-DPG) level in the parent cells or EVs. The metabolic activity can also be assessed as the rate of metabolism of one of the following, including but not limited to, acetylsalicylic acid, n-acetylcystein, 4-aminophenol, azathioprine, bunolol, captopril, chlorpromazine, dapsone, daunorubicin, dehydroepiandrosterone, didanosin, dopamine, epinephrine, esmolol, estradiol, estrone, etoposide, haloperidol, heroin, insulin, isoproterenol, isosorbide dinitrate, ly 217896, 6-mercaptopurine, misonidazole, nitroglycerin, norepinephrine, para-aminobenzoic acid. In some aspects, the identity of the EVs (e.g., exosomes) is assessed by partitioning of a substrate by the complexes, e.g., by mass spectrometry, chemiluminescence, fluorescence spectroscopy, or absorbance spectroscopy. The substrate can comprise acetazolamide, arbutine, bumetamide, creatinine, darstine, desethyldorzolamide, digoxigenin digitoxoside, digoxin-16'-glucuronide, epinephrine, gentamycin, hippuric acid, metformin, norepinephrine, p-aminohippuric acid, papaverine, penicillin g, phenol red, serotonin, sulfosalicylic acid, tacrolimus, tetracycline, tucaresol, vancomycin, or any combination thereof.

In some aspects, the identity of the EVs (e.g., exosomes) can be assessed and/or validated based on their basic physical properties (e.g., size, mass, volume, diameter, buoyancy, density) and/or membrane properties (e.g., viscosity, deformability fluctuation, fluidity). Non-limiting examples of other properties that can be used to assess and/or validate the EVs (e.g., exosomes) are provided below. See also WO 2019/183678 A1, WO 2019/099942 A1, and International Appl. No. PCT/US2018/047937, each of which is incorporated herein by reference in its entirety.

In some aspects, EVs (e.g., exosomes) useful for the present disclosure have a diameter between about 20-300 nm. In certain aspects, an EV (e.g., exosome) has a diameter between about 20-290 nm, 20-280 nm, 20-270 nm, 20-260 nm, 20-250 nm, 20-240 nm, 20-230 nm, 20-220 nm, 20-210 nm, 20-200 nm, 20-190 nm, 20-180 nm, 20-170 nm, 20-160 nm, 20-150 nm, 20-140 nm, 20-130 nm, 20-120 nm, 20-110 nm, 20-100 nm, 20-90 nm, 20-80 nm, 20-70 nm, 20-60 nm, 20-50 nm, 20-40 nm, 20-30 nm, 30-300 nm, 30-290 nm, 30-280 nm, 30-270 nm, 30-260 nm, 30-250 nm, 30-240 nm, 30-230 nm, 30-220 nm, 30-210 nm, 30-200 nm, 30-190 nm, 30-180 nm, 30-170 nm, 30-160 nm, 30-150 nm, 30-140 nm, 30-130 nm, 30-120 nm, 30-110 nm, 30-100 nm, 30-90 nm, 30-80 nm, 30-70 nm, 30-60 nm, 30-50 nm, 30-40 nm, 40-300 nm, 40-290 nm, 40-280 nm, 40-270 nm, 40-260 nm, 40-250 nm, 40-240 nm, 40-230 nm, 40-220 nm, 40-210 nm, 40-200 nm, 40-190 nm, 40-180 nm, 40-170 nm, 40-160 nm, 40-150 nm, 40-140 nm, 40-130 nm, 40-120 nm, 40-110 nm, 40-100 nm, 40-90 nm, 40-80 nm, 40-70 nm, 40-60 nm, 40-50 nm, 50-300 nm, 50-290 nm, 50-280 nm, 50-270 nm, 50-260 nm, 50-250 nm, 50-240 nm, 50-230 nm, 50-220 nm, 50-210 nm, 50-200 nm, 50-190 nm, 50-180 nm, 50-170 nm, 50-160 nm, 50-150 nm, 50-140 nm, 50-130 nm, 50-120 nm, 50-110 nm, 50-100 nm, 50-90 nm, 50-80 nm, 50-70 nm, 50-60 nm, 60-300 nm, 60-290 nm, 60-280 nm, 60-270 nm, 60-260 nm, 60-250 nm, 60-240 nm, 60-230 nm, 60-220 nm, 60-210 nm, 60-200 nm, 60-190 nm, 60-180 nm, 60-170 nm, 60-160 nm, 60-150 nm, 60-140 nm, 60-130 nm, 60-120 nm, 60-110 nm, 60-100 nm, 60-90 nm, 60-80 nm, 60-70 nm, 70-300 nm, 70-290 nm, 70-280 nm, 70-270 nm, 70-260 nm, 70-250 nm, 70-240 nm, 70-230 nm, 70-220 nm, 70-210 nm, 70-200 nm, 70-190 nm, 70-180 nm, 70-170 nm, 70-160 nm, 70-150 nm, 70-140 nm, 70-130 nm, 70-120 nm, 70-110 nm, 70-100 nm, 70-90 nm, 70-80 nm, 80-300 nm, 80-290 nm, 80-280 nm, 80-270 nm, 80-260 nm, 80-250 nm, 80-240 nm, 80-230 nm, 80-220 nm, 80-210 nm, 80-200 nm, 80-190 nm, 80-180 nm, 80-170 nm, 80-160 nm, 80-150 nm, 80-140 nm, 80-130 nm, 80-120 nm, 80-110 nm, 80-100 nm, 80-90 nm, 90-300 nm, 90-290 nm, 90-280 nm, 90-270 nm, 90-260 nm, 90-250 nm, 90-240 nm, 90-230 nm, 90-220 nm, 90-210 nm, 90-200 nm, 90-190 nm, 90-180 nm, 90-170 nm, 90-160 nm, 90-150 nm, 90-140 nm, 90-130 nm, 90-120 nm, 90-110 nm, 90-100 nm, 100-300 nm, 110-290 nm, 120-280 nm, 130-270 nm, 140-260 nm, 150-250 nm, 160-240 nm, 170-230 nm, 180-220 nm, or 190-210 nm. The size of the EV (e.g., exosome) described herein can be measured by methods known in the art, such as microscopy or by automated instrumentation, e.g., a hematological analysis instrument or by resistive pulse sensing.

In some aspects, an EV (e.g., exosome) comprises a bi-lipid membrane ("EV membrane") comprising an interior surface and an exterior surface. In certain aspects, the interior surface faces the inner core (i.e., lumen) of the EV. In certain aspects, the exterior surface can be in contact with the endosome, the multivesicular bodies, or the membrane/cytoplasm of a producer cell or a target cell.

In some aspects, the EV membrane comprises lipids and fatty acids. In some aspects, the EV membrane comprises phospholipids, glycolipids, fatty acids, sphingolipids, phosphoglycerides, sterols, cholesterols, and phosphatidylserines.

In some aspects, the EV membrane comprises an inner leaflet and an outer leaflet. The composition of the inner and outer leaflet can be determined by transbilayer distribution assays known in the art, see, e.g., Kuypers et al., *Biochim Biophys Acta* 819:170 (1985). In some aspects, the composition of the outer leaflet is between approximately 70-90% choline phospholipids, between approximately 0-15% acidic phospholipids, and between approximately 5-30% phosphatidylethanolamine. In some aspects, the composition of the inner leaflet is between approximately 15-40% choline phospholipids, between approximately 10-50% acidic phospholipids, and between approximately 30-60% phosphatidylethanolamine.

In some aspects, the EV membrane comprises a polysaccharide, such as glycan.

In some aspects, EVs (e.g., exosomes) have been engineered to express one or more exogenous biologically active molecules. In certain aspects, the one or more exogenous biologically active molecules comprises a payload. Non-limiting examples of payloads that can be introduced into an EV include agents such as, nucleotides (e.g., nucleotides comprising a detectable moiety or a toxin or that disrupt transcription), nucleic acids (e.g., DNA or mRNA molecules that encode a polypeptide such as an enzyme, or RNA molecules that have regulatory function such as miRNA, dsDNA, lncRNA, or siRNA), amino acids (e.g., amino acids comprising a detectable moiety or a toxin that disrupt translation), polypeptides (e.g., enzymes), lipids, carbohydrates, and small molecules (e.g., small molecule drugs and toxins). In some aspects, a payload comprises a therapeutic molecule, adjuvant, immune modulator, or any combination thereof.

In some aspects, a payload is a therapeutic molecule. In certain aspects, a therapeutic molecule comprises an antigen, which is capable of inducing an immune response in a subject (e.g., tumor antigen, self-antigen, antigen derived from a virus, fungus, protozoa, bacteria, or any combination thereof), viral vector (e.g., AAV), peptides, concatenated peptides, or any combination thereof. In some aspects, the therapeutic molecule comprises an antibody or antigen-binding portion thereof. In certain aspects, the antibody or antigen-binding fragment thereof comprises a scFv, scFab, scFab-Fc, nanobody, or any combination thereof. In some aspects, the antibody or antigen-binding fragment thereof comprises an agonist antibody, blocking antibody, a targeting antibody, a fragment thereof, or a combination thereof.

In some aspects, a payload is an adjuvant. As used herein, the term "adjuvant" refers to any substance that enhances the therapeutic effect of the payload (e.g., increasing an immune response to the antigen). Non-limiting examples of adjuvants include: Stimulator of Interferon Genes (STING) agonist, a toll-like receptor (TLR) agonist, an inflammatory mediator, and combinations thereof.

In some aspects, a payload is an immune modulator. In certain aspects, an immune modulator has anti-tumor activity (e.g., an immune checkpoint inhibitor). In other aspects, an immune modulator has tolerogenic activity. In some aspects, an immune modulator can regulate innate immune response. In certain aspects, an immune modulator regulates innate immune response by targeting natural killer cells. In some aspects, an immune modulator can regulate adaptive immune response. In some aspects, the immune modulator regulates adaptive immune response by targeting cytotoxic T cells. In further aspects, the immune modulator regulates adaptive immune response by targeting B cells. In certain aspects, an immune modulator comprises a cytokine. In some aspects, the cytokine is IL-12.

In some aspects, the one or more exogenous biologically active molecules comprises a targeting moiety. In certain aspects, the targeting moiety is specific to an organ, tissue, cell, or any combination thereof. Non-limiting examples of cells that can be targeted with the EVs (e.g., exosomes) include: a tumor cell, dendritic cell, T cell, B cell, neutrophils, myeloid-derived suppressor cell (MDSC, e.g., a monocytic MDSC or a granulocytic MDSC), monocyte, macrophage, NK cell, platelets, neuron, hepatocyte, hematopoietic stem cell, adipocytes, basophil, eosinophil, or any combination thereof. Non-limiting examples of tissues that can be targeted with EVs (e.g., exosome) of the present disclosure include a liver, heart, lungs, brain, kidneys, central nervous system, peripheral nervous system, muscle, bone, blood, spleen, lymph nodes, stomach, esophagus, bladder, colon, pancreas, thyroid, salivary gland, adrenal gland, pituitary, breast, skin, ovary, uterus, prostate, testis, or any combination thereof.

In some aspects, an EV (e.g., exosome) further comprises one or more scaffold moieties, which are capable of anchoring the exogenous biologically active molecules to the EV (e.g., exosome) (e.g., either on the luminal surface or on the exterior surface). In some aspects, the scaffold moieties anchor or link the exogenous biologically active molecules to the EV. In certain aspects, scaffold moieties are polypeptides ("exosome proteins"). In other aspects, scaffold moieties are non-polypeptide moieties. In some aspects, exosome proteins include various membrane proteins, such as transmembrane proteins, integral proteins and peripheral proteins, enriched on the exosome membranes. They can include various CD proteins, transporters, integrins, lectins, and cadherins. In certain aspects, a scaffold moiety (e.g., exosome protein) comprises Scaffold X. In other aspects, a scaffold moiety (e.g., exosome protein) comprises Scaffold Y. In further aspects, a scaffold moiety (e.g., exosome protein) comprises both a Scaffold X and a Scaffold Y.

In some aspects, an EV (e.g., exosome) comprises a linker that link one or more exogenous biologically active molecules to the EVs. In certain aspects, the exogenous biologically active molecules are linked to the EVs (e.g., exosomes) directly or via one or more scaffold moieties (e.g., Scaffold X or Scaffold Y). As used herein, the term "linker" refers to a peptide or polypeptide sequence (e.g., a synthetic peptide or polypeptide sequence) or to a non-polypeptide, e.g., an alkyl chain. In some aspects, two or more linkers can be linked in tandem. When multiple linkers are present, each of the linkers can be the same or different. Generally, linkers provide flexibility or prevent/ameliorate steric hindrances. Linkers are not typically cleaved; however in certain aspects, such cleavage can be desirable. Accordingly, in some aspects, a linker can comprise one or more protease-cleavable sites, which can be located within the sequence of the linker or flanking the linker at either end of the linker sequence.

In some aspects, the linker is a peptide linker. In some aspects, the peptide linker can comprise at least about two, at least about three, at least about four, at least about five, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 amino acids.

In some aspects, the peptide linker is synthetic, i.e., non-naturally occurring. In one aspect, a peptide linker includes peptides (or polypeptides) (e.g., natural or non-naturally occurring peptides) which comprise an amino acid sequence that links or genetically fuses a first linear sequence of amino acids to a second linear sequence of amino acids to which it is not naturally linked or genetically fused in nature. For example, in one aspect the peptide linker can comprise non-naturally occurring polypeptides which are modified forms of naturally occurring polypeptides (e.g., comprising a mutation such as an addition, substitution or deletion).

Linkers can be susceptible to cleavage ("cleavable linker") thereby facilitating release of the exogenous biologically active molecule (e.g., antigen, adjuvant, or immune modulator).

In some aspects, the linker is a "reduction-sensitive linker." In some aspects, the reduction-sensitive linker contains a disulfide bond. In some aspects, the linker is an "acid labile linker." In some aspects, the acid labile linker contains hydrazone. Suitable acid labile linkers also include, for example, a cis-aconitic linker, a hydrazide linker, a thiocarbamoyl linker, or any combination thereof.

In some aspects, the linker comprises a non-cleavable linker.

II.F. EV (e.g., Exosome) Production

In some aspects, the present disclosure is also directed to the production of EVs (e.g., exosomes) using the one or more chromatography operational parameters (e.g., binding parameters) and/or chromatography reagents identified with the high-throughput methods disclosed herein. In certain aspects, the one or more chromatography operational parameters (e.g., binding parameters) and/or chromatography reagents identified with the methods disclosed herein are optimal for producing EVs (e.g., exosomes) of interest. As described herein, a chromatography operational parameters (e.g., binding parameter) and/or chromatography reagent is "optimal" for producing EVs (e.g., exosomes), where the chromatography operational parameters (e.g., binding parameter) and/or chromatography reagent improves one or more properties of an EV (e.g., exosome). For example, in some aspects, an EV (e.g., exosome) produced using the one or more optimal chromatography operational parameters (e.g., binding parameters) and/or chromatography reagents described herein have increased ligand density ("EV ligand density") compared to a reference (e.g., an EV produced using different chromatography operational parameters (e.g., binding parameters) and/or chromatography reagents). In certain aspects, the ligand density of an EV (e.g., exosome) produced using the one or more optimal chromatography operational parameters (e.g., binding parameters) and/or chromatography reagents described herein is increased by at least about 5%, at least about 10%, at least about 20%, at least about 30%, at least about 40%, at least about 50%, at least about 60%, at least about 70%, at least about 80%, at least about 90%, or at least about 100% or more compared to a reference (e.g., an EV produced using different chromatography operational parameters (e.g., binding parameters) and/or chromatography reagents). In some aspects, the ligand density of an EV (e.g., exosome) produced using the one or more chromatography operational parameters (e.g., binding parameters) and/or chromatography reagents identified with the methods disclosed herein is at least about 5 ligands/EV, at least about 10 ligands/EV, at least about $10^2$ ligands/EV, at least about $10^3$ ligands/EV, at least about $10^4$ ligands/EV, at least about $10^5$ ligands/EV, or at least about $10^6$ ligands/EV.

In certain aspects, a method of producing EVs (e.g., exosomes) comprises obtaining the EV (e.g., exosomes) from a producer cell, wherein the producer cell contains one or more components of the EV (e.g., exosome) (e.g., exogenous biologically active molecules); and purifying the obtained EV (e.g., exosome) using the one or chromatography operational parameters (e.g., binding parameters) and/or chromatography reagents described herein. In some aspects, the method comprises: modifying a producer cell by introducing one or more components of an EV disclosed herein (e.g., exogenous biologically active molecules); obtaining the EV (e.g., exosome) from the modified producer cell; and purifying the obtained EV (e.g., exosome) using the one or chromatography operational parameters (e.g., binding parameters) and/or chromatography reagents described herein. In further aspects, the method comprises: obtaining an EV (e.g., exosome) from a producer cell; purifying the obtained EV using the one or chromatography operational parameters (e.g., binding parameters) and/or chromatography reagents described herein; and modifying the purified EV (e.g., exosome). In certain aspects, the method further comprises formulating the isolated EV into a pharmaceutical composition.

Methods of Modifying a Producer Cell or an EV (e.g., Exosome)

As described herein, in some aspects, a method of producing an EV (e.g., exosome) comprises modifying a producer cell with one or more moieties (e.g., payload and/or targeting moiety). In some aspects, the one or more moieties further comprise a scaffold moiety disclosed herein (e.g., Scaffold X or Scaffold Y).

In some aspects, the producer cell can be a mammalian cell line, a plant cell line, an insect cell line, a fungi cell line, or a prokaryotic cell line. In certain aspects, the producer cell is a mammalian cell line. Non-limiting examples of mammalian cell lines include: a human embryonic kidney (HEK) cell line, a Chinese hamster ovary (CHO) cell line, an HT-1080 cell line, a HeLa cell line, a PERC-6 cell line, a CEVEC cell line, a fibroblast cell line, an amniocyte cell line, an epithelial cell line, a mesenchymal stem cell (MSC) cell line, and combinations thereof. In certain aspects, the mammalian cell line comprises HEK-293 cells, BJ human foreskin fibroblast cells, fHDF fibroblast cells, AGE.HN® neuronal precursor cells, CAP® amniocyte cells, adipose mesenchymal stem cells, RPTEC/TERT1 cells, or combinations thereof. In some aspects, the producer cell is a primary cell. In certain aspects, the primary cell can be a primary mammalian cell, a primary plant cell, a primary insect cell, a primary fungi cell, or a primary prokaryotic cell.

In some aspects, the producer cell is not an immune cell, such as an antigen presenting cell, a T cell, a B cell, a natural killer cell (NK cell), a macrophage, a T helper cell, or a regulatory T cell (Treg cell). In other aspects, the producer cell is not an antigen presenting cell (e.g., dendritic cells, macrophages, B cells, mast cells, neutrophils, Kupffer-Browicz cell, or a cell derived from any such cells).

In some aspects, the one or more moieties can be a transgene or mRNA, and introduced into the producer cell by transfection, viral transduction, electroporation, extrusion, sonication, cell fusion, or other methods that are known to the skilled in the art.

In some aspects, the one or more moieties is introduced to the producer cell by transfection. In some aspects, the one or more moieties can be introduced into suitable producer cells using synthetic macromolecules, such as cationic lipids and polymers (Papapetrou et al., *Gene Therapy* 12: S118-S130 (2005)). In some aspects, the cationic lipids form complexes with the one or more moieties through charge interactions. In some of these aspects, the positively charged complexes bind to the negatively charged cell surface and are taken up by the cell by endocytosis. In some other aspects, a cationic polymer can be used to transfect producer cells. In some of these aspects, the cationic polymer is polyethylenimine (PEI). In certain aspects, chemicals such as calcium phosphate, cyclodextrin, or polybrene, can be used to introduce the one or more moieties to the producer cells. The one or more moieties can also be introduced into a producer cell using a physical method such as particle-mediated transfection, "gene gun", biolistics, or particle bombardment technology (Papapetrou et al., *Gene Therapy* 12: S118-S130 (2005)). A reporter gene such as, for example, beta-galactosidase, chloramphenicol acetyltransferase, luciferase, or green fluorescent protein can be used to assess the transfection efficiency of the producer cell.

In certain aspects, the one or more moieties are introduced to the producer cell by viral transduction. A number of viruses can be used as gene transfer vehicles, including moloney murine leukemia virus (MMLV), adenovirus, adeno-associated virus (AAV), herpes simplex virus (HSV), lentiviruses, and spumaviruses. The viral mediated gene transfer vehicles comprise vectors based on DNA viruses, such as adenovirus, adeno-associated virus and herpes virus, as well as retroviral based vectors.

In certain aspects, the one or more moieties are introduced to the producer cell by electroporation. Electroporation creates transient pores in the cell membrane, allowing for the introduction of various molecules into the cell. In some aspects, DNA and RNA as well as polypeptides and non-polypeptide therapeutic agents can be introduced into the producer cell by electroporation.

In certain aspects, the one or more moieties introduced to the producer cell by microinjection. In some aspects, a glass micropipette can be used to inject the one or more moieties into the producer cell at the microscopic level.

In certain aspects, the one or more moieties are introduced to the producer cell by extrusion.

In certain aspects, the one or more moieties are introduced to the producer cell by sonication. In some aspects, the producer cell is exposed to high intensity sound waves, causing transient disruption of the cell membrane allowing loading of the one or more moieties.

In certain aspects, the one or more moieties are introduced to the producer cell by cell fusion. In some aspects, the one or more moieties are introduced by electrical cell fusion. In other aspects, polyethylene glycol (PEG) is used to fuse the producer cells. In further aspects, sendai virus is used to fuse the producer cells.

In some aspects, the one or more moieties are introduced to the producer cell by hypotonic lysis. In such aspects, the producer cell can be exposed to low ionic strength buffer causing them to burst allowing loading of the one or more moieties. In other aspects, controlled dialysis against a hypotonic solution can be used to swell the producer cell and to create pores in the producer cell membrane. The producer cell is subsequently exposed to conditions that allow resealing of the membrane.

In some aspects, the one or more moieties are introduced to the producer cell by detergent treatment. In certain aspects, producer cell is treated with a mild detergent which transiently compromises the producer cell membrane by creating pores allowing loading of the one or more moieties. After producer cells are loaded, the detergent is washed away thereby resealing the membrane.

In some aspects, the one or more moieties introduced to the producer cell by receptor mediated endocytosis. In certain aspects, producer cells have a surface receptor which upon binding of the one or more moieties induces internalization of the receptor and the associated moieties.

In some aspects, the one or more moieties are introduced to the producer cell by filtration. In certain aspects, the producer cells and the one or more moieties can be forced through a filter of pore size smaller than the producer cell causing transient disruption of the producer cell membrane and allowing the one or more moieties to enter the producer cell.

In some aspects, the producer cell is subjected to several freeze thaw cycles, resulting in cell membrane disruption allowing loading of the one or more moieties.

Alternatively, a method of producing an EV (e.g., exosome) can comprise modifying an EV directly by introducing one or more moieties (e.g., payload, targeting moiety, and/or scaffold moiety) into the EV. In some aspects, the one or more moieties can be introduced directly into an EV (e.g., exosome) with any of the methods described above for modifying a producer cell.

Methods of Purifying an EV (e.g., Exosome)

In some aspects, a method of producing an EV (e.g., exosome) comprises isolating the EV from a sample (e.g., producer cells) using one or more chromatography operational parameters (e.g., binding parameters) and/or reagents identified with the high-throughput methods disclosed herein. As described herein, in certain aspects, EVs (e.g., exosomes) are purified using a chromatography. Non-limiting examples of chromatography include size exclusion chromatography, affinity chromatography, ion-exchange chromatography, mixed-mode chromatography, hydrophobic interaction chromatography, reversed-phase chromatography, hydroxyapatite chromatography, immobilized metal affinity chromatography, or any combination thereof. In certain aspects, the chromatography is size exclusion chromatography (e.g., size exclusion high-performance liquid chromatography (SEC-HPLC)). In further aspects, the chromatography is ion-exchange chromatography. In certain aspects, the ion-exchange chromatography is a strong cation exchange chromatography. In further aspects, the chromatography is an anion exchange high-performance liquid chromatography (AEX-HPLC). In certain aspects, the chromatography is an ion-pairing reversed-phase chromatography (IPRP-HPLC).

In some aspects, the chromatography operational parameters (e.g., binding parameters) and/or chromatography reagents identified with the present disclosure are optimal for isolating the EVs from a sample (e.g., producer cells) because they can improve one or more aspects of the purification process. For example, in some aspects, the chromatography operational parameters (e.g., binding parameters) and/or chromatography reagents identified with the present disclosure can improve EV (e.g., exosome) yield, increase EV (e.g., exosome) ligand density, and/or decrease impurity recovery. Accordingly, in some aspects, the present disclosure provides a method of purifying an EV (e.g., exosome) from a sample to improve an EV yield, improve EV ligand density, and/or reduce impurity recovery, the method comprising: (i) contacting the sample to a chromatography resin or medium under a plurality of chromatography operational parameters (e.g., binding parameters), (ii) collecting a fraction comprising the EV from (i), and (iii) determining an EV yield, impurity recovery, and/or EV ligand density from (ii). As described herein, in certain aspects, the EV is subjected to the chromatography resin or medium or to the one or more chromatography reagents. In some aspects, subjecting the EV to the chromatography resin or medium or to the one or more chromatography reagents can improve EV yield, increase EV ligand density, and/or reduce impurity recovery.

In some aspects, the one or more optimal chromatography operational parameters (e.g., binding parameters) and/or chromatography reagents identified with the methods disclosed herein can be used to increase a ligand density of an EV (e.g., exosome). In certain aspects, a method of increasing a ligand density of an EV present in a sample comprises contacting the sample to a chromatography resin or medium under the one or more optimal chromatography operational parameters (e.g., binding parameters) and/or chromatography reagents identified with the methods disclosed herein. In some aspects, the one or more optimal chromatography operational parameters (e.g., binding parameters) and/or chromatography reagents increases the ligand density on the EV by at least about 5%, at least about 10%, at least about 20%, at least about 30%, at least about 40%, at least about 50%, at least about 60%, at least about 70%, at least about 80%, at least about 90%, at least about 100% or more compared to a reference (e.g., ligand density of a corresponding EV under different chromatography operational parameters (e.g., binding parameters) and/or chromatography reagents or the ligand density of the EV in the sample prior to the contacting).

In some aspects, the one or more optimal chromatography operational parameters (e.g., binding parameters) and/or chromatography reagents identified with the present disclosure can decrease the amount of impurity present in a sample comprising an EV (e.g., exosome). In certain aspects, a method of decreasing an amount of impurity in a sample comprising an extracellular vesicle (EV), the method comprising contacting the sample to a chromatography resin or medium under the one or more optimal chromatography operational parameters (e.g., binding parameters) and/or chromatography reagents, wherein the one or more optimal chromatography operational parameters (e.g., binding parameters) and/or chromatography reagents decrease the amount of impurity in a sample. In some aspects, the amount of impurity is decreased by at least about %, at least about 10%, at least about 20%, at least about 30%, at least about 40%, at least about 50%, at least about 60%, at least about 70%, at least about 80%, at least about 90% or more compared to a reference (e.g., amount of impurity present in a sample using different chromatography operational parameters (e.g., binding parameters) and/or chromatography reagents or the amount of impurity present in the sample prior to the contacting).

In some aspects, the purity of a composition comprising an EV (e.g., exosome) directly affects the potency of the EV (e.g., exosome). See FIG. 4. In certain aspects, the potency of an EV increases as the purity of the EV increases. Accordingly, in some aspects, the one or more optimal chromatography operational parameters (e.g., binding parameters) and/or chromatography reagents identified with the high-throughput methods disclosed herein can increase the potency of an EV by decreasing the amount of impurity present in a sample comprising the EV. In certain aspects, the methods disclosed herein can increase the potency of an EV by at least about 5%, at least about 10%, at least about 20%, at least about 30%, at least about 40%, at least about 50%, at least about 60%, at least about 70%, at least about 80%, at least about 90% or more compared to a reference (e.g., potency of an EV present in a sample using different chromatography operational parameters (e.g., binding parameters) and/or chromatography reagents or the potency of the EV present in the sample prior to the contacting in step (i)). As described herein, in certain aspects, the present disclosure can decrease the amount of both soluble and particulate impurities present in a sample comprising an EV.

In some aspects, the one or more optimal chromatography operational parameters (e.g., binding parameters) and/or chromatography reagents can be used to increase the EV (e.g., exosome) yield of a sample. In certain aspects, a method of increasing an extracellular vesicle (EV) yield in a sample, the method comprising contacting the sample to a chromatography resin or medium under the one or more optimal chromatography operational parameters (e.g., binding parameters) and/or chromatography reagents identified in the present disclosure, wherein the optimal chromatography operational parameters (e.g., binding parameters) and/or chromatography reagents increase the EV yield of the sample. In certain aspects, the EV yield is increased by at least about 5%, at least about 10%, at least about 20%, at least about 30%, at least about 40%, at least about 50%, at least about 60%, at least about 70%, at least about 80%, at least about 90%, at least about 100% or more compared to a reference (e.g., EV yield of a sample under different chromatography operational parameters (e.g., binding parameters) and/or chromatography reagents or the EV yield of the sample prior to the contacting).

As described supra, in some aspects, a method of purifying an EV (e.g., exosome) disclosed herein can further comprise (iv) adjusting at least one of the plurality of chromatography operational parameters (e.g., binding parameters) and repeating steps (i) to (iii) of the high-throughput methods disclosed herein. In certain aspects, the adjusting step of (iv) and the steps of (i) to (iii) are repeated until the desired level of EV yield, EV ligand density, and/or impurity recovery is obtained.

In some aspects, the methods disclosed herein can be used in combination with other methods known in the art for purifying an EV (e.g., exosome) from a sample. Accordingly, it is contemplated that all known manners of isolation of EVs are deemed suitable for use herein. For example, physical properties of EVs can be employed to separate them from a medium or other source material, including separation on the basis of electrical charge (e.g., electrophoretic separation), size (e.g., filtration, molecular sieving, etc.), density (e.g., regular or gradient centrifugation), Svedberg constant (e.g., sedimentation with or without external force, etc.). Isolation can also be based on one or more biological properties, and include methods that can employ surface markers (e.g., for precipitation, reversible binding to solid phase, FACS separation, specific ligand binding, non-specific ligand binding, affinity purification etc.).

Isolation and enrichment can be done in a general and non-selective manner, typically including serial centrifugation. Alternatively, isolation and enrichment can be done in a more specific and selective manner, such as using EV or producer cell-specific surface markers. For example, specific surface markers can be used in immunoprecipitation, FACS sorting, affinity purification, and magnetic separation with bead-bound ligands.

In some aspects, size exclusion chromatography can be utilized to isolate the EVs. Size exclusion chromatography techniques are known in the art. In some aspects, a void volume fraction is isolated and comprises the EVs of interest. Further, in some aspects, the EVs can be further isolated after chromatographic separation by centrifugation techniques (of one or more chromatography fractions), as is generally known in the art. In some aspects, for example, density gradient centrifugation can be utilized to further isolate the extracellular vesicles. In certain aspects, it can be desirable to further separate the producer cell-derived EVs from EVs of other origin. For example, the producer cell-derived EVs can be separated from non-producer cell-derived EVs by immunosorbent capture using an antigen antibody specific for the producer cell.

In some aspects, the isolation of EVs can involve combinations of methods that include, but are not limited to, differential centrifugation, size-based membrane filtration, immunoprecipitation, FACS sorting, and magnetic separation.

The practice of the present disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986);); Crooke, Antisense drug Technology: Principles, Strategies and Applications, 2nd Ed. CRC Press (2007) and in Ausubel et al. (1989) Current Protocols in Molecular Biology (John Wiley and Sons, Baltimore, Md.).

All of the references cited above, as well as all references cited herein, are incorporated herein by reference in their entireties.

The following examples are offered by way of illustration and not by way of limitation.

EXAMPLES

Example 1

High-Throughput Screening Method

To identify the different chromatography operational parameters that are relevant in the purification of EVs (e.g., exosomes) from a sample, a high-throughput screening method was developed. FIG. 1 provides a schematic of an example of the operational processing component of the high-throughput process development described herein. As shown, chromatographic resin slurried in a buffer solution was aliquoted into the wells of a 96-well filter plate. The resin wells were equilibrated with the buffer solution, vortexed at 1,600 rpm, and centrifuged at 1,750 RPM to remove any excess buffer. The load material (i.e., comprising EVs and impurities) was then transferred to the resin wells, and incubated for 20 minutes under vortex to approach equilibrium binding conditions. The load material was then centrifuged through the filter plate, and collected as flowthrough for analysis. This load step can be repeated as many times as required to achieve the target mass challenge. Following the load, the unbound load material was flushed away using additional equilibration buffer. The resin was then eluted in elution buffer, and subsequently stripped with a column strip solution. As described elsewhere in the present disclosure, in some aspects, additional steps (e.g., wash or cleaning step) can also be performed. As shown in FIG. 1, in each phase of the process (e.g., equilibrium phase, load phase, flush phase, elution phase, and strip phase), a sample can be obtained and analyzed using any of the analytical methods described herein.

Example 2

Comparison of Binding Conditions for PTGFRN::GFP Exosomes and IL12::PTGFRN Exosomes Over Poros XS Chromatography Column To assess how the different components of an EV (e.g., exosome) can affect purification conditions, the performance of PTGFRN::GFP exosomes (i.e., expressing GFP conjugated to PTGFRN protein) and IL12::PTGFRN exosomes (i.e., expressing IL-12 conjugated to PTGFRN protein) over Poros XS in weak-partitioning and flow through binding conditions was assessed. Two parameters, pH and sodium ion concentration ($[Na^+]$) were evaluated in full factorial (n=48). Equilibrated resins were challenged to 5E11 particles/mL resin, a non-saturated equilibrium binding condition, and incubated for 20 minutes under vigorous shaking (1600 RPM). Unbound material was collected from resins through a 0.45 μm PVDF filter plate.

Exosome yield was calculated by comparison of resin flowthrough particle counts to load particle counts by Nanoparticle Tracking Analysis. In addition to exosome yield, recovery of an exosome-specific signal was also measured. In the case of PTGFRN::GFP exosomes, luminal GFP was quantified using fluorescence spectroscopy. Recovery of total IL12 protein was evaluated for IL12::PTGFRN exosomes using an IL12-specific Alphalisa assay. The selectivity for ligand density was measured for each condition.

Figure 2:
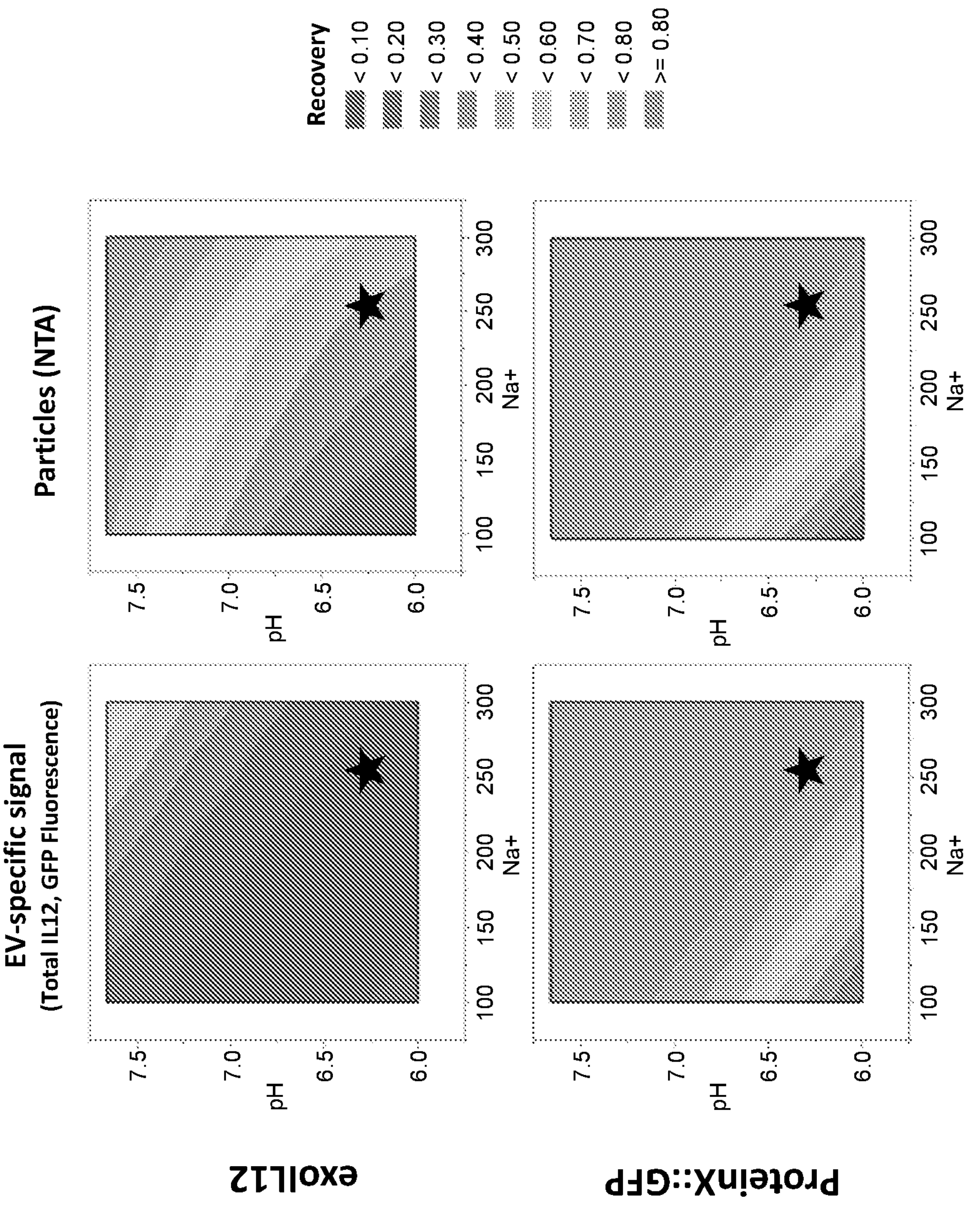
FIG. 2 provides a comparison of EV yield and EV-specific signal observed for two different exosomes employing weak-partitioning and flowthrough chromatography conditions using a Poros XS chromatography resin. The chromatography resin was contacted with an impure exosome preparation in conditions using a plurality of two separate binding parameters, pH (y-axis) and sodium ion concentration ([$Na^+$]) (x-axis). The contacting fluid was then removed from the resin and subjected to analysis. The top row shows the results for an exosome comprising IL-12 conjugated to a Scaffold X moiety (i.e., PTGFRN). The bottom row shows the results for an exosome comprising PTGFRN and loaded with GFP. In both the top and bottom rows, the EV-specific signal is shown on the left and the EV yield is shown on the right. The star represents the suitable operational condition for a platform process involving the binding parameters tested.

As shown in FIG. 2, for PTGFRN::GFP exosomes, there was a direct correlation between the GFP signal and the exosome yield for all pH and [$Na^+$]. This finding indicates that GFP is distributed consistently across the particle population and/or did not different appreciably in properties that could be resolved by chromatography with Poros XS. Regarding IL12::PTFGRN exosomes, the opposite was observed. There was no significant correlation between exosome yield and IL12 signal. This suggested that Poros XS had sub-fractionated populations of exosomes with variable amounts of IL12 fusion protein per particle.

Example 3

High-Throughput Screening of Chromatography Resins for Exosome Purification

Figure 3A:
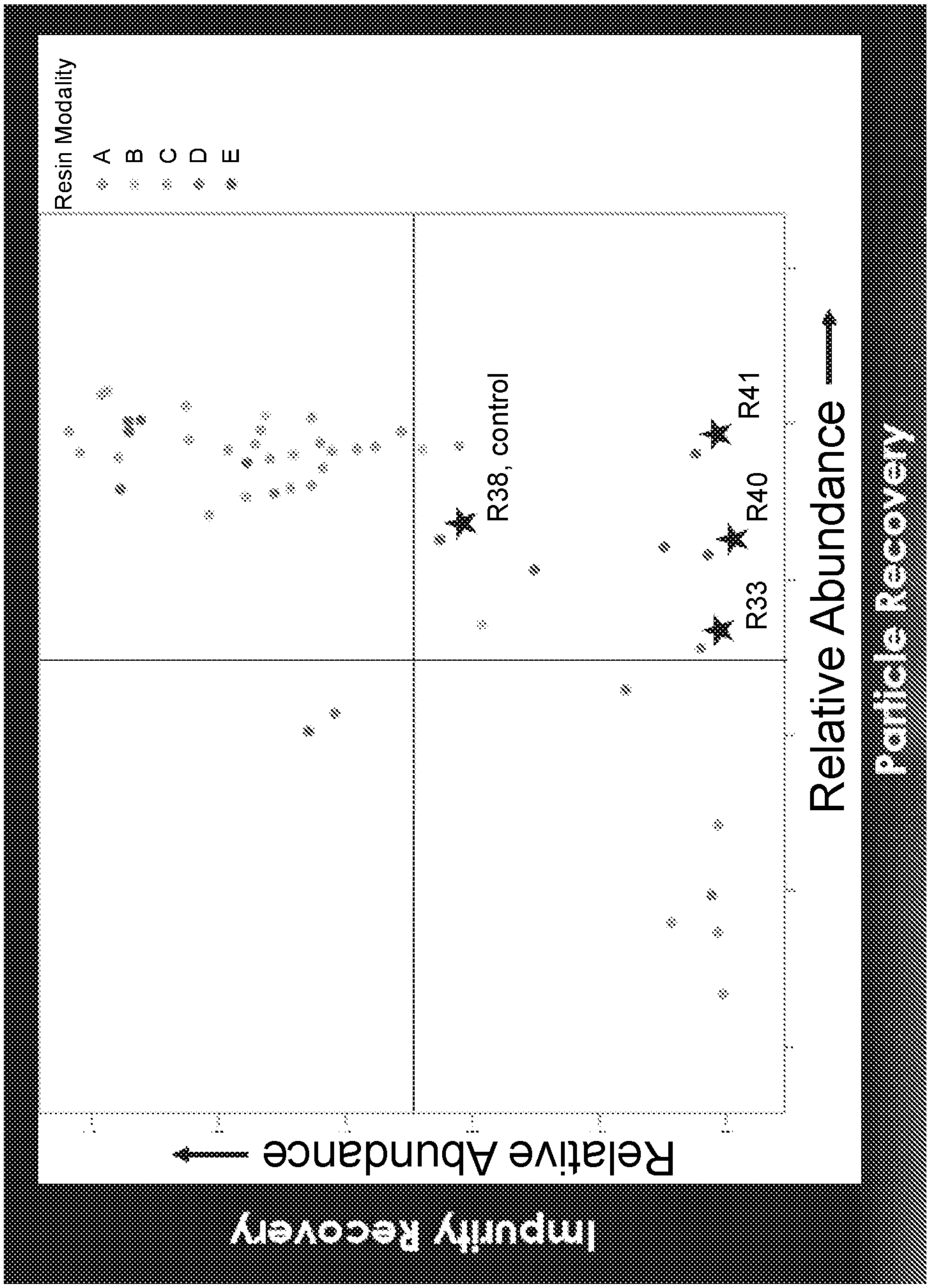
FIGS. 3A and 3B provide a comparison of the capability of different chromatography resins to purify engineered exosomes.

To identify reagents that can be used in flow through or weak partitioning chromatography to reduce impurity, maintain exosome ligand density, and be amenable to integrated processing during exosome purification, a total of 48 different chromatography resins were screened for their capability to bind an engineered exosome Briefly, the 48 resin were equilibrated and challenged to 5E11 particles/mL resin, a non-saturated equilibrium binding condition. The flowthrough fractions were then collected for analysis. As shown in FIG. 3A, an initial comparison of exosome yield and impurity recovery with the 48 resins identified four resin leads (i.e., resins R38, R33, R40, and R41). The lead resins were further assessed with the high-throughput screening methods disclosed herein. Specifically, impurity recovery and recovery of ligand-specific signal of the exosomes were assessed using flowthrough and weak-partitioning mode using a full factorial of pHs and sodium concentrations as described in Example 1.

Figure 3B:
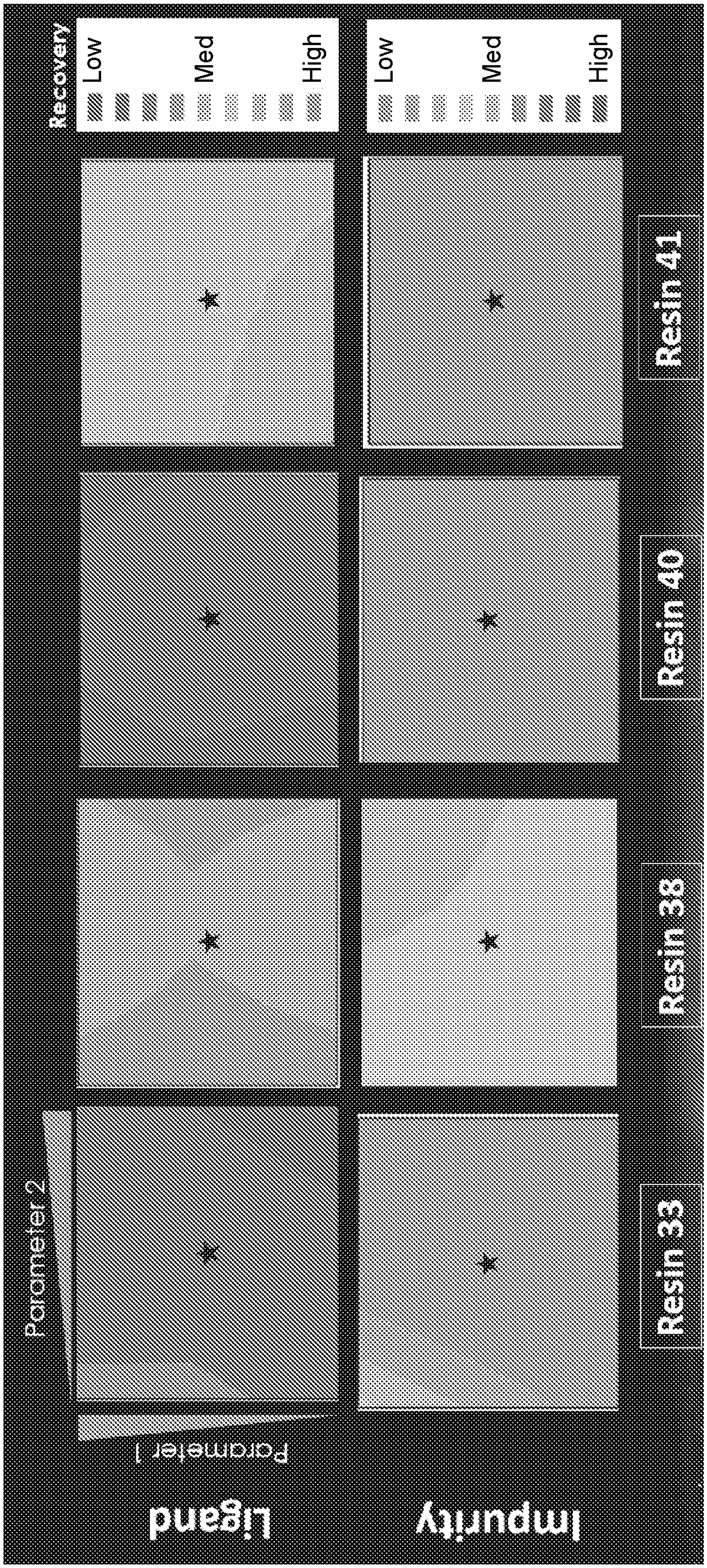

As shown in FIG. 3B, for the parameters tested, regions of highest impurity removal generally resulted in lower ligand yield. However, among the four resins tested, resin 38 resulted in good ligand yield and impurity removal. The results demonstrate that the high-throughput methods disclosed herein can be effectively used to screen rapidly chromatography operational parameters (e.g., binding parameters) and/or reagents for the purification of EV (e.g., exosomes) from a sample using chromatography.

Example 4

Analysis of EV Purity on the Potency of the EVs (e.g., Exosomes)

Figure 4:
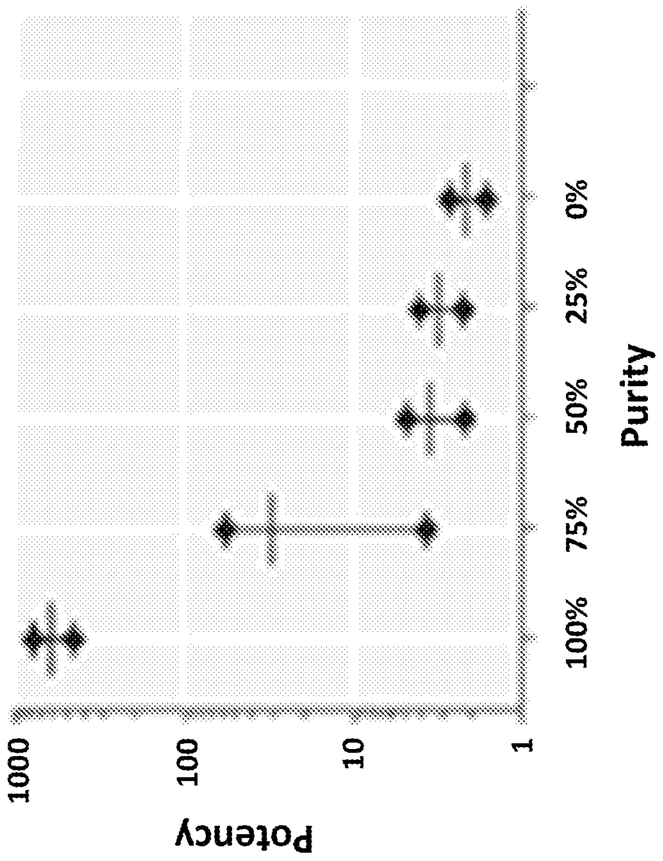
FIG. 4 provides a comparison between the purity (x-axis) of an EV comprising composition and the potency (y-axis) of the EV.

The high-throughput methods described herein (e.g., see Examples 2 and 3) were used to compare the effect of purity on the potency of the EVs. As shown in FIG. 4, there was a direct relationship between the potency of EVs and the purity of the composition comprising the EVs. At 75% purity, there was a loss in potency of nearly 96%. This data further demonstrates the value of the high-throughput methods described herein, which can rapidly identify optimal chromatography operational parameters (e.g., binding parameters) and/or chromatography reagents that can be used to reduce the amount of impurities present in a sample comprising EVs (e.g., exosomes).

Example 5

High-Throughput Screening of a DNA Removal Wash

The high-throughput methods described herein (see, e.g., Example 1) were used to identify wash buffers that could selectively desorb bound DNA impurity from an anion-exchange (AEX) membrane Each well of a 96-well plate-format anion exchange membrane device was equilibrated with a buffered solution of Tris at pH 7.4 with sodium chloride (hereafter referred to as "equilibration buffer"). After equilibration, each well was treated with exosome-containing cell culture fluid to a load challenge of 5E11 particles/mL resin, a non-saturated equilibrium binding condition. Non-bound species were removed from the membranes using additional equilibration buffer.

Loaded membranes were then subjected to DNA wash buffer screening using different wash buffer solutions as shown in FIG. 5A. Wash buffers were incubated on the surface of the membranes for five minutes, and then collected individually as fractions for analysis. AEX membranes were subsequently washed with equilibration buffer prior to elution of the AEX membranes with a Tris-buffered solution at pH 7.4 with increased sodium chloride relative to the load condition. The elutions were collected as fractions and subjected to analysis.

Figure 5B:
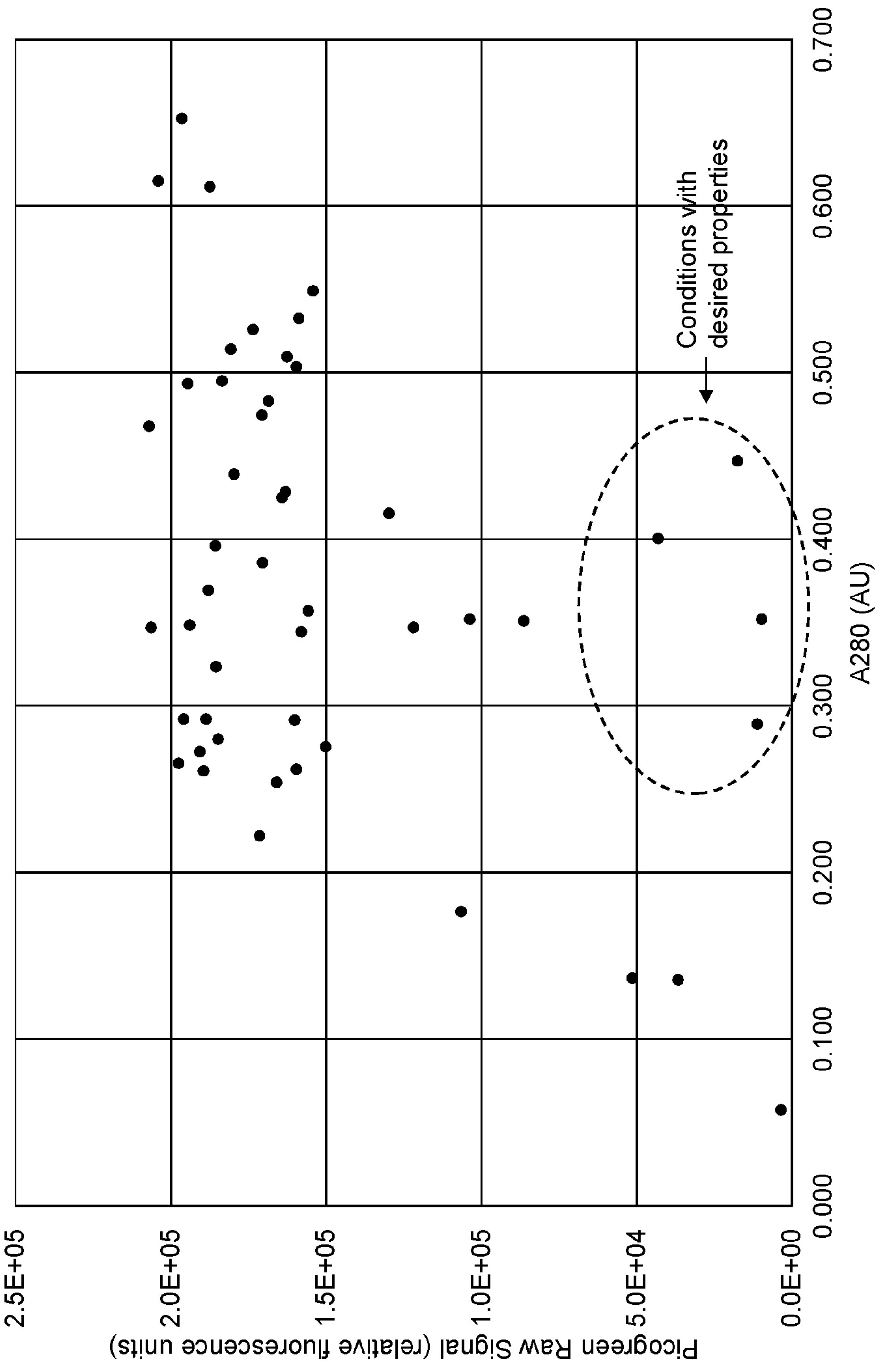

Residual DNA was assessed in the AEX eluates using the Quant-iT™ PicoGreen™ dsDNA (Picogreen) assay, and EV yield was assessed using absorbance at 280 nm (A280). Wash buffers with the desired selectivity resulted in elution fractions exhibiting reduced Picogreen signal with accompanying high A280. (FIG. 5B).

Example 6

High Throughput Screening to Identify Selective Removal of a Protein Impurity from an Engineered Exosome The high-throughput methods described herein (e.g., Example 1) were used to evaluate impurity selectivity across an experimental space using a mixed-mode chromatography media with engineered exosomes. Two chromatographic parameters affecting binding were screened: pH and [NaCl]. Chromatography media was equilibrated and challenged to 5E11 particles/mL resin, a non-saturated equilibrium binding condition, and incubated for 20 minutes with agitation. The unbound material was then collected as flowthrough fractions.

Exosome yield was calculated by comparison of resin flowthrough particle counts to load particle counts by absorbance at 280 nm (A280) (FIG. 6A) and SEC-HPLC intrinsic fluorescence (FIG. 6B). In addition to exosome yield, recovery of an ligand-specific signal was also measured using an AlphaLisa assay (FIG. 6C).

A proteoglycan impurity found in exosome preparations was measured in each condition of the high throughput screen using an proteoglycan-specific AlphaLisa assay. Impurity recovery is shown in FIG. 6D. Chromatographic operational regions with highest selectivity for exosomes with high amounts of ligand can be determined by comparing the recoveries of exosomes and ligand relative to recovery of the proteoglycan impurity.

Example 7

High-Throughput Screen for the Removal of Free ASOs

Next, the high-throughput screening methods described herein was used to identify suitable chromatography operational parameters and/or chromatography reagents that can be used to remove free (i.e., not conjugated to EVs) ASOs after the exogenous loading of ASOs onto EVs (e.g., exosomes).

Figure 7:
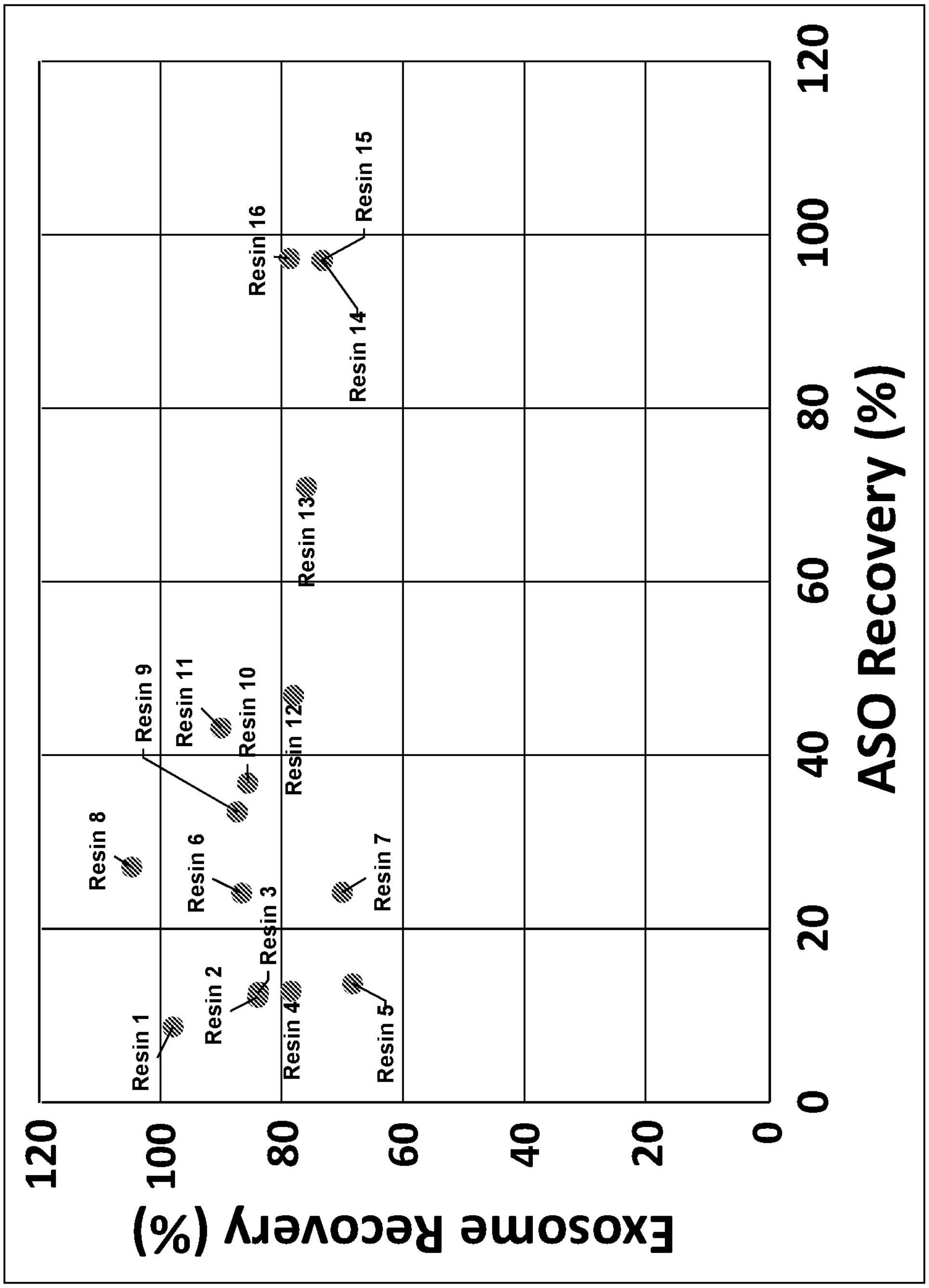
FIG. 7 provides the results from high-throughput screening (HTS) of 16 beaded resins in 96-well plate format for removal of free antisense oligonucleotides (ASOs) (x-axis) and recovery of exosomes (y-axis). The resins tested are numbered based on the amount of free ASOs removed (1=highest free ASO removal; and 16=lowest free ASO removal).

Briefly, to identify suitable resins for the removal of free ASOs from a sample, 16 different beaded resins were slurried in a buffer (50% v/v slurry) and aliquoted into separate wells of a 96-well filter plate. The resin wells were equilibrated with the buffer solution, shaken, and centrifuged to remove any excess buffer. The load material (i.e., free ASO (≤500 μM) or only exosomes (≤$5\times10^{12}$ p/mL)) was transferred to the resin wells, mixed for an extended period of time, and subsequently centrifuged through the filter plate. The flowthrough filtrate was collected for further analysis. To ensure adequate volumetric recovery, equilibration buffer was added to the resin wells, mixed, and centrifuged through the filter plate. The wash filtrate was collected separately for further analysis. ASO recovery was determined by measuring the absorbance at 260 nm for a load with only free ASO (≤500 μM) and resulting flowthrough (FT)/wash fractions. Exosome recovery was determined by measuring the dynamic light scattering (DLS) intensity at a fixed attenuation for a load with only exosomes (≤$5\times10^{12}$ p/mL) and resulting FT/wash fractions. Based on the results provided in FIG. 7, four resins (i.e., Resins 1, 2, 3, and 4) were selected based on their high free ASO removal (<20% recovered in FT/wash) and acceptable exosome yield (>60%) under the loading condition tested.

Figure 8:
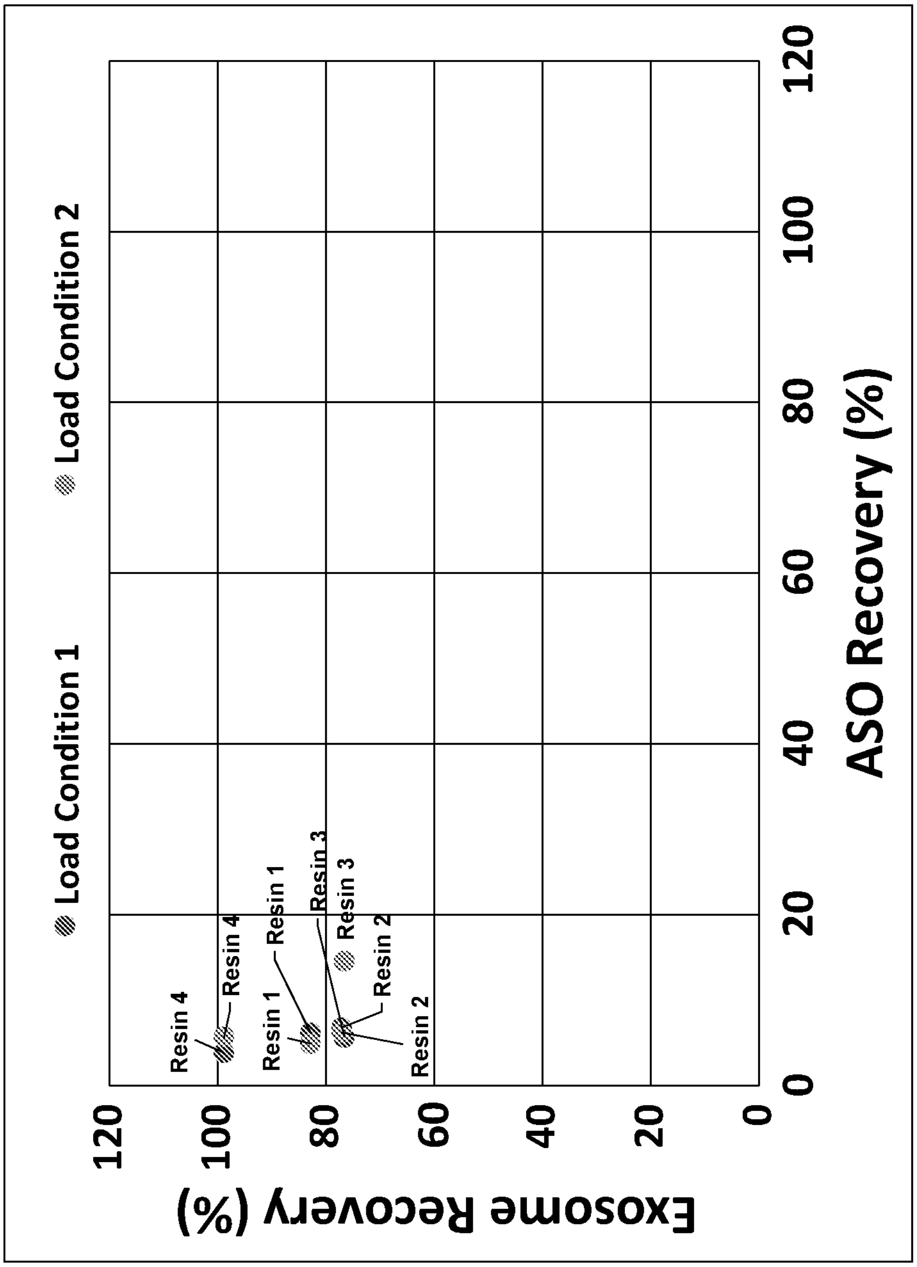
FIG. 8 provides the results from high-throughput screening (HTS) of 4 beaded resins in 96-well plate format for removal of free antisense oligonucleotides (ASOs) and recovery of free exosomes under two separate loading conditions. The loading conditions differed in the NaCl and sucrose concentrations, i.e., compared to loading condition 1, loading condition 2 had higher NaCl concentration but lower sucrose concentration. The beaded resins are those identified in FIG. 8 as being optimal resins for free ASO removal (i.e., Resins 1, 2, 3, and 4). ASO recovery was determined by measuring the absorbance at 260 nm for a load with only free ASO (≤500 μM) and resulting flowthrough (FT)/wash fractions. Exosome recovery was determined by measuring the dynamic light scattering (DLS) intensity at a fixed attenuation for a load with only exosomes (≤$5\times10^{12}$ p/mL) and resulting flowthrough (FT)/wash fractions. Each of the circles represent resins 1, 2, 3, or 4 under either load condition 1 (dark gray circle) or load condition 2 (light gray circle).

Next, to identify suitable loading conditions for the removal of free ASOs from a sample, the four resins identified above (i.e., Resins 1, 2, 3, and 4) were used under two different loading conditions, which varied in NaCl (ranged between about 50-150 mM) and sucrose (ranged between about 2.5-5.0% w/v) concentrations. Loading condition 1 had low NaCl concentration and high sucrose concentration. Loading condition 2 had high NaCl concentration and low sucrose concentration. As shown in FIG. 8, under the different loading conditions, the capability of the four resins tested to remove free ASO and recover the EVs (e.g., exosomes) was similar.

The above results demonstrate that the methods disclosed herein can be useful in identifying chromatography operational parameters and/or reagents that are suitable for purification of molecules of interest (e.g., EVs, e.g., exosomes) from a sample.

INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

EQUIVALENTS

While various specific aspects have been illustrated and described, the above specification is not restrictive. It will be appreciated that various changes can be made without departing from the spirit and scope of the disclosure(s). Many variations will become apparent to those skilled in the art upon review of this specification.

What is claimed is:

1. A method of purifying an extracellular vesicle (EV) comprising a prostaglandin F2 receptor negative regulator (PTGFRN) protein or a fragment thereof expressed in or on the EV from a sample, the method comprising (i) contacting the sample to an ion-exchange chromatography resin, a size exclusion chromatography resin, an ion-exchange chromatography medium, or a size exclusion chromatography medium, wherein the resin or medium is not a mixed mode chromatography resin or medium, under a plurality of chromatography operational parameters, (ii) collecting a fraction comprising the EV from step (i), and (iii) determining an EV yield, impurity recovery, and/or EV ligand density from step (ii), wherein the contacting of the sample to the resin or medium occurs in a microplate or in miniature columns, and wherein the PTGFRN protein or fragment thereof anchors a payload or an exogenous biologically active molecule to the EV.

2. A method of identifying one or more chromatography operational parameters suitable for purifying an extracellular vesicle (EV) comprising a prostaglandin F2 receptor negative regulator (PTGFRN) protein or a fragment thereof expressed in or on the EV from a sample comprising the EV and an impurity with a chromatography, the method comprising:

(i) contacting the sample to an ion-exchange chromatography resin, a size exclusion chromatography resin, an ion-exchange chromatography medium, or a size exclusion medium, wherein the resin or medium is not a mixed mode chromatography resin or medium, under a plurality of chromatography operational parameters, (ii) collecting a fraction comprising the EV from step (i), (iii) determining an EV yield, impurity recovery, and/or EV ligand density from step (ii), and (iv) identifying the one or more chromatography operational parameters, wherein the one or more identified chromatography operational parameters are suitable for purifying the EV from the sample if (a) the EV yield is increased, (b) the impurity recovery is reduced, and/or (c) the EV ligand density is increased, as compared to a corresponding value in the sample prior to step (i), wherein the contacting of the sample to the resin or medium occurs in a microplate or in miniature columns, and wherein the PTGFRN protein or fragment thereof anchors a payload or an exogenous biologically active molecule to the EV.

3. The method of claim 1, wherein the collecting of the fraction in (ii) is performed under a flow through mode, bind and elute mode, or weak-partition mode.

4. The method of claim 1, further comprising (iv) adjusting at least one of the chromatography operational parameters and repeating steps (i) to (iii), if (a) the EV yield is decreased, (b) the impurity recovery is increased, and/or (c) the EV ligand is decreased, as compared to a desired corresponding value.

5. The method of claim 1, wherein the chromatography operational parameters comprise a plurality of pHs, a plurality of weak acids and/or conjugate bases, a plurality of alcohols, a plurality of carbohydrates, a plurality of detergents, a plurality of chaotropic agents, a plurality of kosmotropic agents, a plurality of mass challenge, a plurality of residence time, a plurality of temperatures, a plurality of salt concentrations, a plurality of buffers, or any combination thereof.

6. The method of claim 5, wherein: (i) the plurality of pHs is about 3, about 4, about 5, about 6, about 7, about 8, about 9, about 10, about 11, about 12, or about 13; (ii) the plurality of salt concentrations is between about 0 M to about 4 M; or (iii) both (i) and (ii).

7. The method of claim 1, wherein the EV yield is determined by one or more of the following:

(1) measuring an EV particle count of the fraction in (ii);
(2) measuring an absorbance of the fraction in (ii);
(3) measuring an intrinsic fluorescence of the fraction in (ii);
(4) measuring a light scattering emission signal of the fraction in (ii);
(5) measuring a turbidity of the fraction in (ii);
(6) measuring a static light obscuration of the fraction in (ii); and
(7) measuring a static refractive index of the fraction in (ii).

8. The method of claim 7, wherein:

(a) the light scattering emission signal is generated using an excitation wavelength ranging from about 280 nm to 700 nm and is detected by measuring an emission wavelength that is 0-20 nm longer or shorter than the excitation wavelength and ranging from 260 nm to 720 nm;
(b) the absorbance is measured at a wavelength from about 200 nm to about 1,100 nm;
(c) the intrinsic fluorescence is measured at an excitation wavelength of about 460 nm and an emission wavelength of about 470 nm; or
(d) any combination of (a) to (c).

9. The method of claim 1, wherein the impurity recovery is determined using an assay comprising an ELISA, Alphalisa, flow cytometry, Western blot, immunoprecipitation, fluorescence spectroscopy, chemiluminescence, mass spectrometry, absorbance spectroscopy, polymerase chain reaction (PCR), or combinations thereof.

10. The method of claim 1, wherein the chromatography resin is Poros XS.

11. The method of claim 1, wherein the sample is derived from a cell culture or from a body fluid of a subject.

12. The method of claim 1, wherein the EV comprises an exosome.

13. The method of claim 1, wherein the EV further comprises a targeting moiety.

14. A method of purifying an extracellular vesicle (EV) from a sample, comprising identifying one or more chromatography operational parameters according to the method of claim 2, and further purifying the EV from the sample using the one or more identified chromatography operational parameters.

15. A method of increasing a (PTGFRN) protein or fragment density of an extracellular vesicle (EV) present in a sample, the method comprising identifying one or more chromatography operational parameters according to the method of claim 2, and further contacting the sample to a chromatography resin or medium under the one or more identified chromatography operational, wherein the one or more identified chromatography operational parameters are capable of selecting for EVs with high amounts of PTGFRN protein or fragment.

16. A method of decreasing an amount of impurity in a sample comprising an extracellular vesicle (EV), the method comprising identifying one or more chromatography operational parameters according to the method of claim 2, and further contacting the sample to a chromatography resin or medium under the one or more identified chromatography operational parameters, wherein the one or more identified chromatography operational parameters are capable of decreasing the amount of impurity in the sample.

17. A method of increasing an extracellular vesicle (EV) yield in a sample, the method comprising identifying one or more chromatography operational parameters according to the method of claim 2, and further contacting the sample to a chromatography resin or medium under the one or more identified chromatography operational parameters, wherein the one or more identified chromatography operational parameters are capable of increasing the EV yield of the sample.

* * * * *